US011627719B2

(12) United States Patent
Jozefiak et al.

(10) Patent No.: US 11,627,719 B2
(45) Date of Patent: Apr. 18, 2023

(54) PRODUCTION LINE WITH FLOW-THROUGH FEED HEATING AND/OR COOLING SYSTEM AND HEATED SURFACE FOR BREEDING INSECTS, METHOD FOR BREEDING INSECTS AND USES THEREOF

(71) Applicant: HIPROMINE S.A., Robakowo (PL)

(72) Inventors: Damian Jozefiak, Robakowo (PL); Piotr Lubik, Poznan (PL); Krzysztof Dudek, Sedziny (PL)

(73) Assignee: HIPROMINE S.A., Robakowo (PL)

( * ) Notice: Subject to any disclaimer, the term of this patent is extended or adjusted under 35 U.S.C. 154(b) by 0 days.

(21) Appl. No.: 17/857,150

(22) Filed: Jul. 4, 2022

(65) Prior Publication Data

US 2022/0330514 A1 Oct. 20, 2022

Related U.S. Application Data

(63) Continuation of application No. PCT/PL2021/050052, filed on Jul. 5, 2021.

(51) Int. Cl.
*A01K 1/00* (2006.01)
*A01K 67/033* (2006.01)

(52) U.S. Cl.
CPC .......... *A01K 1/0076* (2013.01); *A01K 67/033* (2013.01); *A01K 2227/706* (2013.01)

(58) Field of Classification Search
CPC .............................. A01K 67/033; A01K 1/0076
See application file for complete search history.

(56) References Cited

U.S. PATENT DOCUMENTS

| 2015/0122182 A1* | 5/2015 | Aldana ................ A01K 67/033 119/6.6 |
| 2016/0219887 A1* | 8/2016 | Vickerson ............ A01K 67/033 |
| 2016/0381841 A1* | 12/2016 | Peterson ................ F28D 15/00 165/104.34 |
| 2018/0168133 A1 | 6/2018 | Taylor |

OTHER PUBLICATIONS

PCT Written Opinion of the International Search Authority, dated Sep. 29, 2021, PCT/PL2021/050052 (PCT Application of this Continuation Application in US).
PCT International Search Report, PCT/PL2021/050052 (PCT Application of this Continuation Application in US).

* cited by examiner

*Primary Examiner* — Monica L Perry
(74) *Attorney, Agent, or Firm* — Harvest IP Law LLP

(57) ABSTRACT

The first object of the invention is a production line for rearing and/or breeding insects and/or larval forms of insects of the order Coleoptera and/or Diptera, characterized in that it comprises: at least one breeding line (14) for breeding insects for laying feed thereon and a flow-through feed heating and/or cooling system (1) with a closed flow of heating-cooling medium for heating/cooling the feed on the breeding line (14). The second object is a method for breeding insects including a step of rearing and/or breeding insects and/or larval forms of insects using a production line according to the invention. A further object is a method for breeding insects using a flow-through feed heating and/or cooling system during the breeding. Another object is the use of a flow-through feed heating and/or cooling system (1) with a closed flow of heating-cooling medium for heating/cooling the feed on the breeding line (14).

17 Claims, 15 Drawing Sheets

A

B

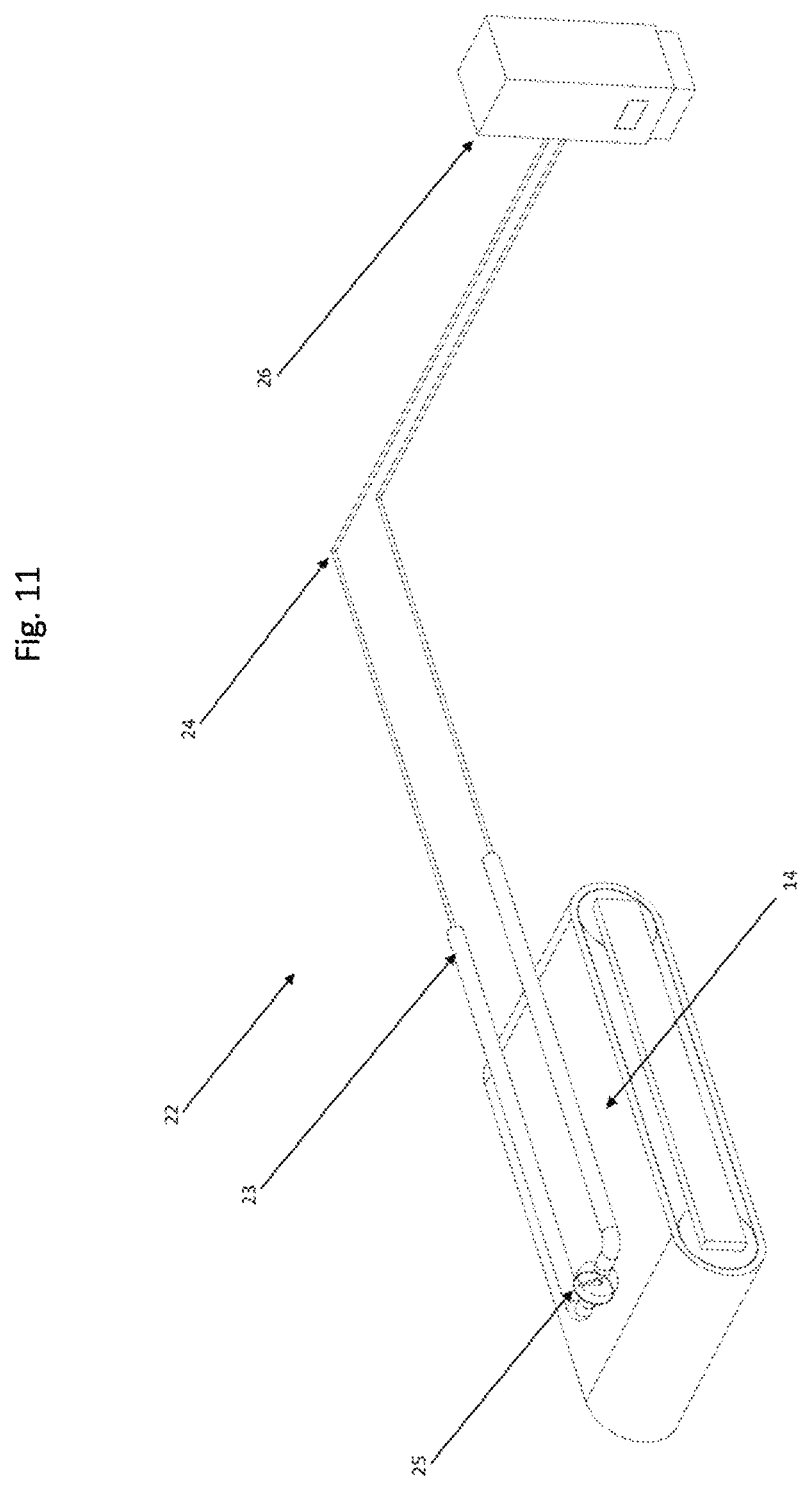

PRODUCTION LINE WITH FLOW-THROUGH FEED HEATING AND/OR COOLING SYSTEM AND HEATED SURFACE FOR BREEDING INSECTS, METHOD FOR BREEDING INSECTS AND USES THEREOF

CROSS REFERENCE TO RELATED APPLICATIONS

This application is a continuation application filed under 35 U.S.C. § 111(a), claiming the benefits under 35 U.S.C. § 120 and § 365(c) of the International Application PCT/PL2021/050052, filed Jul. 5, 2021, which claimed priority to the Polish Patent Application P.435063, filed Aug. 24, 2020 in the Polish Patent Office, the disclosures of which are thereby incorporated by reference.

TECHNICAL FIELD

The object of the invention is a production line for rearing insects and/or larval forms comprising a flow-through feed heating and/or cooling system on a production line, use of a flow-through feed heating and/or cooling system on a production line and a production line for breeding insects, and methods for breeding insects using thereof. Said flow-through feed heating and/or cooling system uses a flow-through heating/cooling in a closed system and a medium in the form of water, glycol or other.

Another object of the invention is a heated production surface for rearing and/or breeding insects and/or larval forms of insects, which uses an electrical heating system, use thereof and a method for breeding using thereof.

The invention using a flow-through feed heating and/or cooling system as well as a production surface heated by an electrical heating system are particularly adapted for rearing and/or breeding insects and/or larval forms of insects of the order Coleoptera and Diptera.

STATE OF ART

In recent years, industrial insect breeding has been indicated as an environmentally sustainable alternative for the production of protein and fat for feed purposes inter alia feeding of livestock and for food purposes (Food and Agriculture Organization of the United Nations 2012 Assessing the potential of insects as food and feed in assuring food security. Summary report. Technical consultation meeting 23-25 January, FAO, Rome, Italy).

A group of insects with a particular potential as a source of protein for feed and food purposes are beetle larvae (Coleoptera) from the darkling beetle family (Tenebrionidae) and hymenopteran larvae (Diptera). Among the species bred on a semi-industrial and industrial scale, species to be mentioned are: lesser mealworm (*Aiphitobius diasperinus*), mealworm (*Tenebrio molitor*), superworm (*Zophobas morio*), confused flour beetle (*Tribolium confusum*), red flour beetle (*Tribolium castaneum*), black flour beetle (*Tribolium madens*), and other species of the darkling beetle family and Hymenoptera from species belonging to the genus Hermetia (*Hermetia illucens*). All the above mentioned species feed in the substrate at the larval growth stage.

Currently used technologies for the breeding of darkling beetle larvae are based on "rack systems", or self-supporting ones using containers with a small surface area with a few centimetres (1-5 cm) thick layer of breeding substrate (described e.g. in the international application PCT WO2014171829A1). As a standard, plastic containers or transport boxes placed on pallets are used for breeding (described e.g. in the application PCT/FR2016/050849). These usually have a small container area, generally not exceeding 0.5 m². Therefore, the solutions used make it difficult to precisely control the microclimate due to poor gas exchange and removal of moisture and excess metabolic heat, etc. Thermal conditions can change dramatically over short periods of time, e.g. due to the temperature of the provided feed or the handling of containers with insects, as well as due to the metabolism of the insects themselves, i.e. so-called specific dynamic heat losses. From the point of view of animal welfare, and especially of insects, which are exothermic animals, unstable environmental conditions are associated with stress and may cause changes in feed intake or growth rates. Drawer and container rearing systems entail the need for heating and/or cooling of the entire room in which the insects are housed. As the species bred belong to thermophilic organisms, the solutions used so far make it necessary to maintain a high air temperature reaching over 30° C. throughout the entire rearing period, which in the case of large-cubature breeding rooms generates high energy consumption, most of which is lost in heating and/or cooling of the air and the room elements themselves and not the insects themselves.

From the Polish patent description PL230275B1, solutions are known in the form of a modular, multi-storey system of technological lines. However, said lines do not use heating and/or cooling of feed.

DISCLOSURE OF INVENTION

The aim of the invention is to overcome the abovementioned disadvantages resulting from the state of the art. This aim has been achieved by unexpectedly observing that the provision of insect feed in the form of heated and/or cooled feed by an engineered flow-through feed heating system and/or cooling placed on and/or under the breeding line based on flow-through heating/cooling in a closed system being a part of an engineered production line or breeding line, allows indirect heating/cooling of insects organisms and their surroundings, thus increases the fattening rate of the insects, at the same time decreases feed consumption per kg of animal body weight gain (FCR) and ensures stabilization of other parameters such as ambient temperature, humidity, thus stabilizing housing parameters and results of insect breeding. This aim has also been achieved by providing a heated production surface for rearing and/or breeding insects and/or larval forms of insects, which comprises an electrical feed heating system for the insect breeding line, which by heating the feed warms the insects and ensures optimum temperature conditions and improves the rearing performance and survival of the insects.

The inventors of the present solution have found that it is preferable to use flow-through heating and/or cooling mounted on breeding lines in order to heat and/or cool the provided feed, which then constitutes a source of heat/cold for the larvae and insects feeding therein. The system allows precise control of thermal conditions in insect breeding, while minimizing energy losses through unnecessary heating/cooling of breeding spaces. Similar effects are obtained when feed is heated by a system of electrical heating of the production surface for rearing and/or breeding insects and/or larval forms of insects.

In both cases where feed is heated/cooled on the breeding line as well as in the case where the heating/cooling system adequately heats/cools the feed on the breeding line the effect of using the system is heating/cooling of feed and thus obtaining stable and optimum conditions for insect breeding, only in one case this happens directly in the feed heating/cooling system on the breeding line and in the other case indirectly in the heating/cooling system of the breeding line from which the feed is then heated/cooled.

A production line for rearing and/or breeding insects and/or larval forms of insects or a breeding line by integration with a flow-through feed heating and/or cooling system or a production surface heated by an electrical heating system, increases the rearing efficiency by providing stable thermal conditions for the insects and insect larvae. In a preferred embodiment the flow-through feed heating and/or cooling system placed directly in the biomass of insects and/or larval forms of insects and feed allows for maintaining relatively low temperature inside the breeding rooms when heating the feed or does not require cooling of the breeding rooms at high breeding room temperatures, because the insects assimilate the necessary heat/cold for their development by taking up the heated/cooled food as well as such a system heats/cools the feed on the breeding line or the breeding line itself and then the feed placed thereon. Thus, a flow-through heating and/or cooling system for feed laid on the line indirectly results in heating/cooling of the animals themselves. Currently, there are no alternative solutions for providing heat/cooling to the larvae and insects themselves in insect production that would not relay on heating/cooling of the breeding rooms and not be associated with significant losses and energy inputs.

The first object of the invention is a production line for rearing and/or breeding insects and/or larval forms of insects, wherein it comprises:
a) at least one breeding line for breeding insects for laying feed thereon,
wherein preferably the breeding line comprises at least one storey (tier), which constitutes an autonomous conveyor belt, preferably with profiled lateral sidewalls arranged bilaterally along the direction of movement of the conveyor belt, preferably the edges of the lateral sidewalls are bent inwards,
b) a flow-through feed heating and/or cooling system with a closed flow of heating-cooling medium for heating and/or cooling the feed on a breeding line, comprises at least one heating-cooling medium supply circuit and at least one heating-cooling medium return circuit connected to each other, and the heating-cooling medium supply circuit and the heating-cooling medium return circuit are fluidly connected to a heat exchanger for heating and/or cooling the heating-cooling medium, and the heating-cooling medium supply circuit and the heating-cooling medium return circuit comprise heating-cooling medium distributors, and heating-cooling pipes of thermally conductive material for the distribution of heat and/or cold on the breeding line are connected to the heating-cooling medium distributor via a shut-off valve, wherein the heating-cooling pipes of thermally conductive material of the system for heating and/or cooling the feed on the breeding line are arranged parallel to the conveyor belt of said at least one breeding line for laying feed for breeding insects thereon, wherein the heating-cooling pipes of thermally conductive material are arranged along the breeding line for rearing insects and are arranged in at least two rows parallel to each other, wherein the heating-cooling medium supply circuit and the heating-cooling medium return circuit are connected via a three-way valve, wherein the rearing and/or breeding of insects and/or larval forms of insects concerns insects of the orders Coleoptera and/or Diptera.

In a preferred embodiment of the flow-through feed heating and/or cooling system, the cooling-heating medium is water or glycol.

In a further preferred embodiment of the production line, the heat exchanger provides heating and/or cooling of the heating-cooling medium to a temperature in the range of 7-50° C., preferably 15-50° C., more preferably 20-48° C., more preferably up to 25-35° C., more preferably up to 28-32° C.

In another preferred embodiment of the production line, the heating-cooling pipes are made of a material with good thermally conductive properties including copper, steel, aluminium, plastic, preferably plastic.

In yet further preferred embodiment of the production line, the heat exchanger is based on a source of electrical energy, gas or the use of heat pumps or heat recuperation.

In a further preferred embodiment of the production line, the heating-cooling pipes are arranged on and/or under the conveyor belt of the breeding line and form at least two rows of heating-cooling pipes spaced from each other, preferably by 20 cm.

In yet another preferred embodiment of the production line, the heating-cooling medium supply circuit and the heating-cooling medium return circuit comprise a system of shut-off valves, drain valves, vents, at least one temperature sensor and at least one pressure sensor, and they are fluidly connected to each other.

In yet further preferred embodiment of the production line, the heating-cooling medium return circuit includes a rotameter.

In a further preferred embodiment of the production line, the heating-cooling medium supply circuit includes a solid particle filter.

In yet further preferred embodiment of the production line, the fluid connection is provided by pipes made of steel.

In another further preferred embodiment of the production line it comprises at least two, preferably several, preferably a dozen, preferably between five and thirty storeys comprising a breeding line and a flow-through feed heating and/or cooling system with a closed flow of the heating/cooling medium.

The second object of the invention is a method for breeding insects including a step of rearing and/or breeding insects and/or larval forms of insects, said step in which the feed is heated and/or cooled by means of a flow-through feed heating and/or cooling system with a closed flow of the heating/cooling medium on a breeding surface and wherein the step of rearing and/or breeding insects and/or larval forms of insects is carried out using a production line as defined in the first object of the invention.

A further object of the invention is a method for breeding insects including the steps:
a) the feed at storage temperature is laid on a breeding line adapted for laying feed for breeding insects thereon,
wherein preferably the breeding line comprises at least one storey, which constitutes an autonomous conveyor belt, preferably with profiled lateral sidewalls arranged bilaterally along the direction of movement of the conveyor belt, preferably the edges of the lateral sidewalls are bent inwards,
b) the feed for insects laid on at least one breeding line adapted for laying feed for insects thereon is heated and/or cooled by a flow-through heating and/or cooling system with a closed flow for heating and/or cooling the feed on the breeding line, wherein the heating and/or cooling system includes:

at least one heating-cooling medium supply circuit and at least one heating-cooling medium return circuit connected to each other, and the heating-cooling medium supply circuit and the heating-cooling medium return circuit are fluidly connected to a heat exchanger for heating and/or cooling the heating-cooling medium, and the heating-cooling medium supply circuit and the heating-cooling medium return circuit comprise the heating-cooling medium distributors, and to the heating-cooling medium distributor via a shut-off valve the heating-cooling pipes of thermally conductive material are connected for distribution of heat/cooling on the breeding line, wherein the heating-cooling pipes of thermally conductive material of the system for heating and/or cooling the feed on the breeding line are arranged parallel to the said at least one breeding line for laying feed for breeding insects thereon, wherein the heating-cooling pipes of thermally conductive material are arranged along the breeding line for insect rearing and are arranged in at least two rows parallel to each other, wherein the heating-cooling medium supply circuit and the heating-cooling medium return circuit are connected via a three-way valve, wherein rearing and/or breeding of insects and/or larval forms of insects concerns insects of the orders Coleoptera and/or Diptera.

In preferred embodiment of the method for breeding insects the feed is heated/cooled to a temperature in the range of 7-50° C., more preferably 15-50° C., more preferably 20-48° C., more preferably to 25-35° C., more preferably to 28-32° C.

In a further preferred embodiment of the method for breeding insects, the bred insects are placed in drawer, box, or self-supporting systems.

In yet further preferred embodiment of the method for breeding insects, the heating-cooling medium is water or glycol.

In a preferred embodiment of the method for breeding insects, the heat exchanger ensures heating/cooling of the heating-cooling medium to a temperature in the range of 7-50° C., more preferably 15-50° C., more preferably 20-48° C., more preferably to 25-35° C., more preferably to 28-32° C.

In an another preferred embodiment of the method for breeding insects, the heating-cooling pipes are made of a material with good thermally conductive properties including copper, steel, aluminium, plastic, preferably plastic.

In yet another preferred embodiment of the method for breeding insects, the heat exchanger is based on a source of electrical energy, gas or the use of heat pumps or heat recuperation.

In a further preferred embodiment of the method for breeding insects, the breeding line comprises at least one storey, which preferably constitutes an autonomous conveyor belt, wherein the heating-cooling pipes are arranged on and/or under the conveyor belt of the breeding line and form at least two rows of heating-cooling pipes and are spaced from each other, preferably by 20 cm.

In yet further preferred embodiment of the method for breeding insects, the heating-cooling medium supply circuit and the heating-cooling medium return circuit include a system of shut-off valves, drain valves, vents, at least one temperature sensor and at least one pressure sensor, and they are fluidly connected to each other.

In a preferred embodiment of the method for breeding insects, the heating-cooling medium return circuit includes a rotameter.

In yet further preferred embodiment of the method for breeding insects, the heating-cooling medium supply circuit includes a solid particle filter.

In a further preferred embodiment of the method for breeding insects, the fluid connection constitutes pipes made of steel.

The invention also relates to the use of a flow-through feed heating and/or cooling system with a closed flow for heating and/or cooling feed on a breeding line for breeding insects, wherein said system includes at least one heating-cooling medium supply circuit and at least one heating-cooling medium return circuit connected to each other, and the heating-cooling medium supply circuit and the heating-cooling medium return circuit are fluidly connected to a heat exchanger for heating and/or cooling the heating-cooling medium, and the heating-cooling medium supply circuit and the heating-cooling medium return circuit comprise the heating-cooling medium distributors, and to the heating-cooling medium distributor via a shut-off valve the heating-cooling pipes of thermally conductive material are connected for distribution of heat/cooling on the breeding line, wherein the heating-cooling pipes of thermally conductive material of the system for heating and/or cooling the feed on the breeding line are arranged parallel to the said at least one breeding line for laying feed for breeding insects thereon, wherein the heating-cooling pipes of thermally conductive material are arranged along the breeding line for insect rearing and are arranged in at least two rows parallel to each other, wherein the heating-cooling medium supply circuit and the heating-cooling medium return circuit are connected via a three-way valve, wherein rearing and/or breeding of insects and/or larval forms of insects concerns insects of the orders Coleoptera and/or Diptera.

In a preferred embodiment of the use of the flow-through feed heating and/or cooling system, water or glycol is used as the heating-cooling medium.

In a further preferred embodiment of the use of the flow-through feed heating and/or cooling system, the heat exchanger provides heating of the heating-cooling medium to a temperature in the range of 7-50° C., more preferably 15-50° C., more preferably 20-48° C., more preferably to 25-35° C., more preferably to 28-32° C.

In a further preferred embodiment of the use of the flow-through feed heating and/or cooling system, pipes made of a material with good thermally conductive properties including copper, steel, aluminium, plastic, preferably plastic are used.

In yet another preferred embodiment of the use of the flow-through feed heating and/or cooling system, a heat exchanger based on a source of electrical energy, gas or the use of heat pumps or heat recuperation is used.

In a preferred embodiment of the use of the flow-through feed heating and/or cooling system, the breeding line comprises at least one storey, which constitutes an autonomous conveyor belt, wherein the heating-cooling pipes arranged on and/or under the conveyor belt of the breeding line which form at least two rows of heating-cooling pipes spaced from each other, preferably by 20 cm, are used.

In yet another preferred embodiment of the use of the flow-through feed heating and/or cooling system, the heating-cooling medium supply circuit and the heating-cooling medium return circuit are used, including a system of shut-off valves, drain valves, vents, at least one temperature sensor and at least one pressure sensor, and they are fluidly connected to each other.

In yet another preferred embodiment of the use of the flow-through feed heating and/or cooling system, the heating-cooling medium return circuit includes a rotameter.

In yet another preferred embodiment of the use of the flow-through feed heating and/or cooling system, the heating-cooling medium supply circuit includes a solid particle filter. In a further preferred embodiment of the use of the flow-through feed heating and/or cooling system, fluid is provided by pipes made of steel.

In a preferred use of the flow-through feed heating and/or cooling system, the system includes at least two, preferably several, preferably a dozen, preferably between five and thirty storeys comprising a breeding line and the flow-through feed heating and/or cooling system with a closed flow of the heating/cooling medium.

Compared to known methods of providing insect larvae with an appropriate level of heat/cooling, the present invention is characterized by a much higher energy efficiency. The greatest advantage is the fact that it is no longer necessary to maintain a high temperature in the breeding rooms for heating the insects or the general cooling of breeding rooms for cooling the insects. The ambient temperature can be in the range of 8° C. to 43° C. Due to the fact that the feed laid on the breeding lines is heated/cooled, the heating-cooling device used can be of much smaller capacity and will consume less energy than in the case of heating/cooling of the entire room.

Another advantage is the speed and efficiency of heating/cooling. The feed in the system is heated in up to 12 hours from a temperature of 8° C. (the temperature of feed stored during cold periods of the year) to a temperature between 20° C. and 48° C., with the possibility of continuously adjusting it to regulate insect metabolism.

A great advantage of the system for heating and/or cooling the feed on the breeding line is also the possibility to adapt the system as well as the breeding line according to the invention to a specific breeding surface, and so it can occupy from 5 to 100% of the total rearing surface. There is no limitation to the size of the production surface, can even cover surfaces of more than 10,000 m$^2$ typical for the largest production halls.

An exemplary flow-through feed heating and/or cooling system in a closed system for heating and/or cooling the feed, which is particularly useful for heating and/or cooling the feed and thus indirectly bred insects, includes the following elements
  a system of pipes of copper, steel, aluminium, plastic or other good thermally conductive material including plastic, distributing the heating-cooling medium and providing heating/cooling for feed.
  a heat exchanger providing heating/cooling of the medium in the pipes thanks to the use of energy from electrical source, gas or based on heat pumps or heat recuperation and other sources of heat allowing to reach a temperature in the range of 7-50° C., more preferably 15-50° C., more preferably 20-48° C., more preferably up to 25-35° C., more preferably up to 28-32° C. allowing to control metabolic processes of insects including specific dynamic heat losses or the removal of excess metabolic heat.
It has proven beneficial to use a flow-through heating and/or cooling system installed on breeding lines in order to heat/cool the provided feed, which then constitutes a source of heat/cooling for the insect larvae feeding therein. The heating and/or cooling system and lines comprising them allow precise control of thermal conditions in insect breeding, while minimizing energy wasted by heating/cooling unnecessary spaces. The possibility of heating the feed using the system and a production line according to the invention can also be used to regulate its moisture due to the increased evaporation of water from the feed of higher temperature. This possibility has important practical consequences, because towards the end of insect fattening it is important to reduce feed moisture, so that the process of sieving insects from the substrate can take place more efficiently. The feed located on the line during fattening of insects has the moisture content of up to 80%, while by using the feed heating and/or cooling system, it is possible to dry it and reduce the moisture content at the end of fattening to a level of 20%. The feed located on the rearing lines is in a layer thickness from 2 to 20 cm depending on the type of feed and species of insect.

Compared to previously used methods of providing insect larvae with an adequate level of heat/cold, the solutions according to the invention using a flow-through heating and/or cooling system installed on breeding lines for heating/cooling the fed feed is characterized by a much higher efficiency. The greatest advantage is that it is not necessary to maintain a high temperature in the breeding rooms when insects need to be warmed up and there is no need to cool down entire breeding rooms when insects need to be cooled down. The ambient temperature can be in the range from 8° C. to 43° C. As only the feed laid on the breeding lines is heated/cooled, the heating-cooling device used can be of a much lower capacity and energy consumption than that used to heat/cool the entire room. In itself, the heating/cooling of feed using a flow-through heating/cooling system installed on the breeding lines is fast and effective. Feed in the system is heated within up to 12 hours from a temperature of 8° C. to a temperature between 20° C. and 48° C., with the possibility of continuously adjusting the temperature to regulate insect metabolism. Research carried out during testing of the prototype system has shown that feed in the described system heats up 6 to 12 times faster than in the open air, which translates into efficiency and speed of use of such a heating system in providing appropriate thermal conditions for insects.

Experiments carried out (Example 5) on *Hermetia illucens* species have shown that insects bred using the technology described herein are characterized by a 7% faster fattening, understood as achieving a 7% higher body weight at the end of the fattening, as well as a 14% reduction in feed conversion ratio (FCR).

The above-mentioned growth parameters as well as the FCR are closely correlated with the vital needs of the insects which have been shown to be 20-300% lower when using direct heating of feed on the breeding lines by a flow-through heating/cooling system. Moreover, the use of heated/cooled feed reduces the stress associated with feeding the larvae/insects and increases their survival, which has been observed to be up to 45% higher when using a flow-through heating and/or cooling system compared to the standard rearing method where entire holding rooms are heated/cooled (Example 5). Thanks to the smooth regulation of the temperature of the fed feed, it is also possible to regulate the insects metabolism level and, if necessary, shorten or lengthen the life cycle, as well as the FCR for both Coleoptera and Diptera insects. The possibility to heat the feed can also be used to regulate its moisture content thanks to the increased evaporation of water from the feed of higher temperature. For the above reasons, another function of the system is the drying of secondary metabolites after insect production including faeces, which are a component of the fertiliser.

An important advantage of production or breeding lines with a flow-through feed heating and/or cooling system as well as a heated production surface with an electrical feed heating system is the fact that such a feed heating and/or cooling system can be used both in multi-level/multi-storey production lines which are the subject of patent PL 230275B1, which increases the available production space as well as when using a single level rearing system or even a "rack system". A great advantage is also the possibility of adapting the flow-through feed heating and/or cooling system as well as the heated production surface with an electrical feed heating system to the breeding surface, so it can occupy from 5 to 100% of the total rearing surface. There is no limitation to the size of the production surface (production or breeding lines with a flow-through feed heating and/or cooling system or an electrical feed heating system), such a heating and/or cooling system can even occupy surfaces of more than 10,000 m² characterizing the largest production halls.

DESCRIPTION OF THE FIGURES OF THE DRAWING

The present invention has been illustrated in figures, which serve only to illustrate examples of the embodiments of the invention and do not limit its scope in any way.

FIG. 11 shows a breeding surface with an electrical feed heating system on the breeding surface.

EMBODIMENTS OF THE INVENTION

The following examples are included only to illustrate the invention and to explain its particular aspects, not to limit it, and should not be equated with the entire scope of the invention as defined in the appended claims.

EXAMPLES

Figure 1:
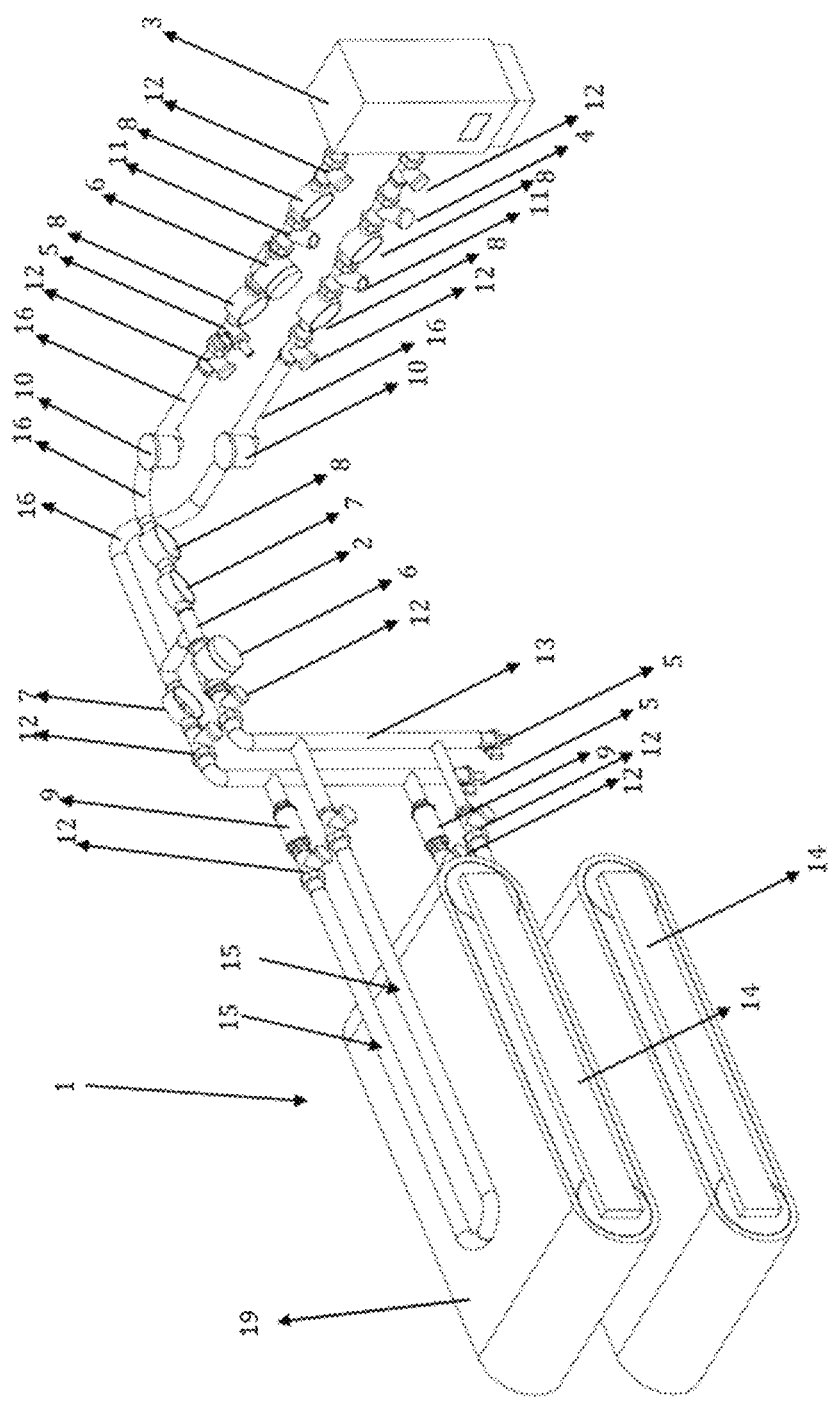
FIG. 1 shows a diagram of the flow-through heating and/or cooling system of the breeding line for breeding invertebrates with heating/cooling on a production line (here above the conveyor belt)
Figure 2:
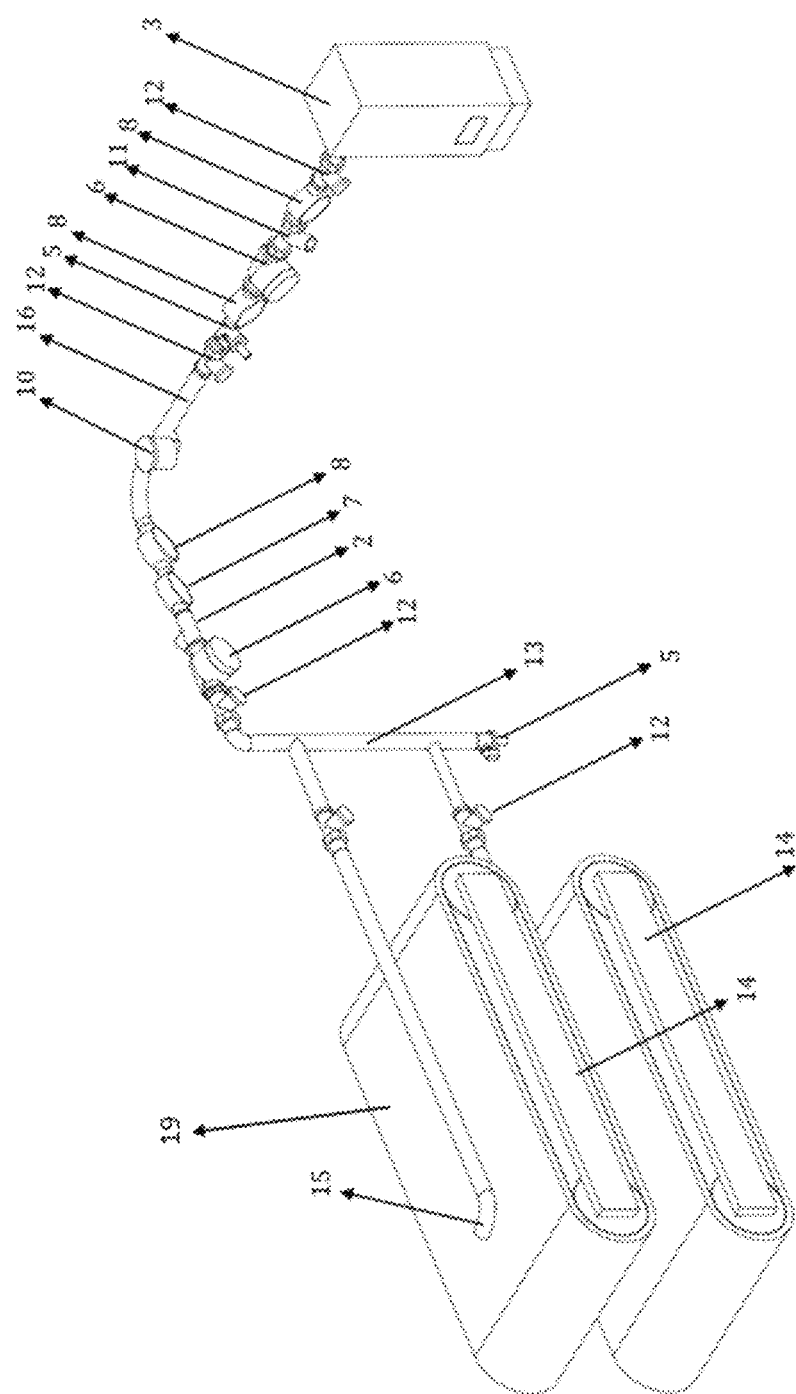
FIG. 2 shows a part of the flow-through heating and/or cooling system with the heated/cooled medium supply circuit.
Figure 3:
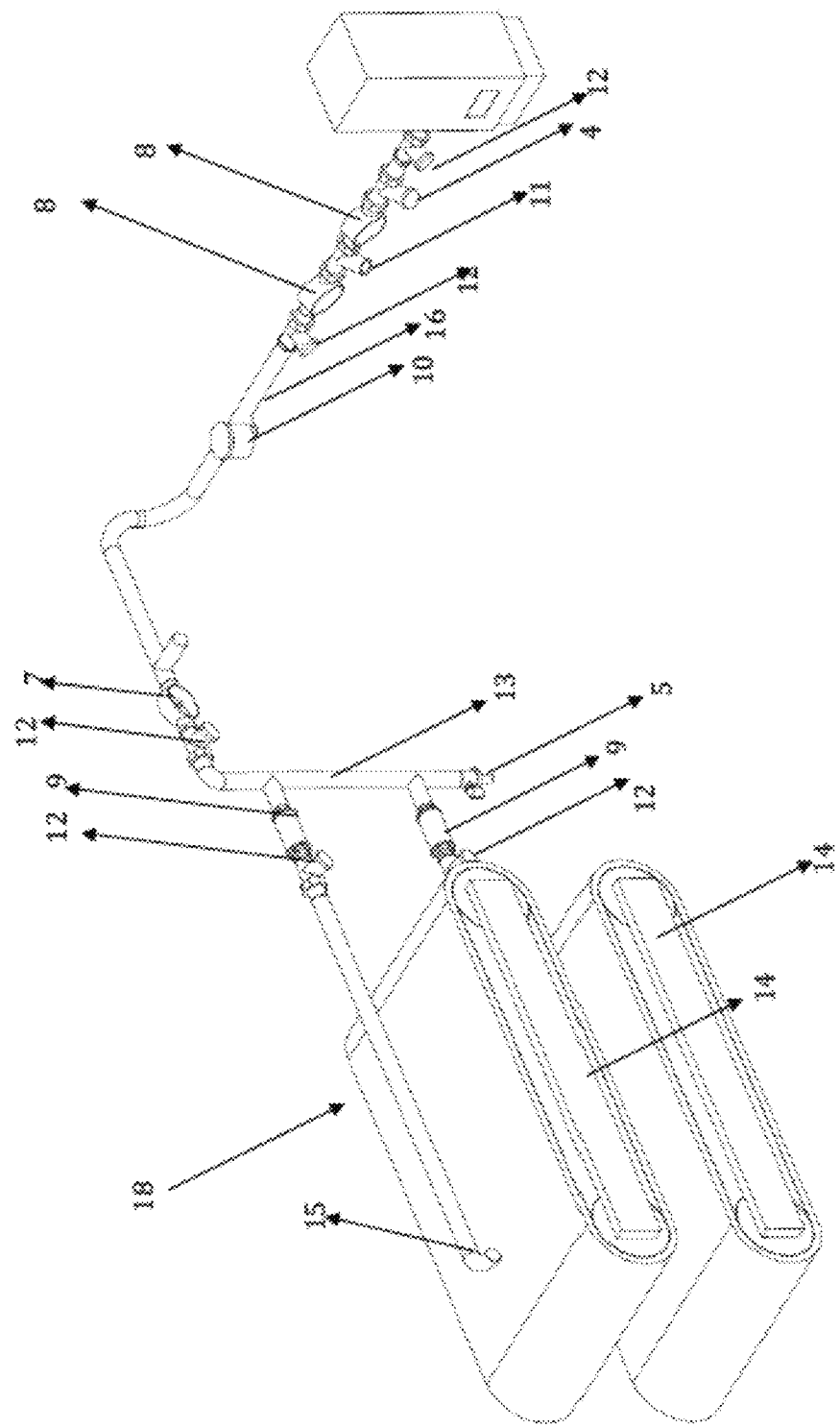
FIG. 3 shows a part of the flow-through heating and/or cooling system with the cooled/heated medium return circuit.

Example 1: Construction of a Flow-Through Feed Heating and/or Cooling System for a Breeding Line for Breeding and Rearing Insects The flow-through feed heating and/or cooling system 1 for heating/cooling feed in insect breeding (FIG. 1) consists of two parts of a closed heating-cooling medium circulation system. The first part of the system (FIG. 2) is connected at the outlet via the shut-off valve 12 to the heat exchanger 3 and constitutes the circuit supplying 17 the system with the heated/cooled heating-cooling medium. The second part of the system constitutes the return circuit 18 (FIG. 3) of the heating-cooling medium and serves to receive the cooled/heated heating-cooling medium and transfer it to the heat exchanger 3, where it is again heated/cooled.

Each part of the system consists of the following constructional elements:

a) a system of heating-cooling pipes 15 e.g., of oxygen-cross-linked polyethylene (PEX) discharging heat/cold from the medium to the feed on breeding lines 14 with a system of shut-off valves 12;

d) a system of filters 11, shut-off valves 12, vents 10;

e) Set of temperature sensors 7 and pressure sensors 8 for heating-cooling medium;

g) heat exchanger 3, as a heat/cold source in the form of e.g., a heat pump or a gas furnace for heating;

h) a system of pipes 16 e.g., of carbon steel supplying the heating-cooling medium from the heat exchanger 3 to the distributor 13, supplying the heating-cooling pipe system with the heating-cooling medium, i) drain valves 5 of heating-cooling medium.

The part supplying the system with heated/cooled heating-cooling medium additionally comprises a drain valve 5, which enables draining the medium e.g. when servicing the line or needing to replace the medium, placed downstream of the first circulation pump 6 and a three-way valve 2 directly connected to upstream of the second circulation pump 6, which enables mixing the medium from both parts of the system in order, e.g. to regulate the pressure or temperature. Whereas the part of the system receiving the cooled/heated heating-cooling medium comprises a balancing valve 4 equalizing pressure, located upstream of the shut-off valve 12 connecting at the outlet of the second part of the system with the heat exchanger 3.

The heating-cooling medium in the flow-through feed heating and/or cooling system in insect breeding was water, heated by a gas furnace as heat exchanger 3. The temperature of water leaving the furnace was 39° C. The heated water was discharged from the furnace through a steel pipe 16 placed in an insulating bundle minimizing heat loss. The intensity of the water flow was 0.16 m³/h. The water, after passing through a solid particle filter 11 (mesh filter), was pumped by a circulation pump 6 to the distributor 13 of the heating-cooling installation placed on the production lines of the breeding line 14 for insect breeding and rearing.

In order to transfer the heat to the feed, heated water is fed from the distributor 13 into a heating-cooling installation consisting of heating-cooling pipes 15 of PEX, which are arranged in two rows 20 cm apart from each other along the breeding line 14 intended for rearing insects. The heating-cooling pipes 15 are suspended directly above the breeding lines 14, onto which the feed for the bred insects is then laid. The laid feed has a temperature lower than the heating-cooling medium and of about 20° C., as a result of which it begins to receive its heat, until it reaches a thermal equilibrium at the level of 39° C., more preferably stabilizing the feed temperature at the level of 28-32° C. The water, cooled to a temperature of about 38° C., returns through the heating-cooling pipe system 15 to the heat exchanger 3 here a heating device maintaining a constant temperature of the medium in the heating-cooling system (a flow-through feed heating and/or cooling system on the breeding line).

Temperature sensors 7 as well as pressure sensors 8 of the heating-cooling medium are placed at specific points in the heating-cooling system, providing information about its physical parameters. A rotameter 9 is also installed at the entry to the breeding lines 14 in order to measure the flow rate of the medium. The gas boiler was provided with an automatic temperature regulation allowing for any temperature setting in the range from 7 to 50° C.

Figure 4:
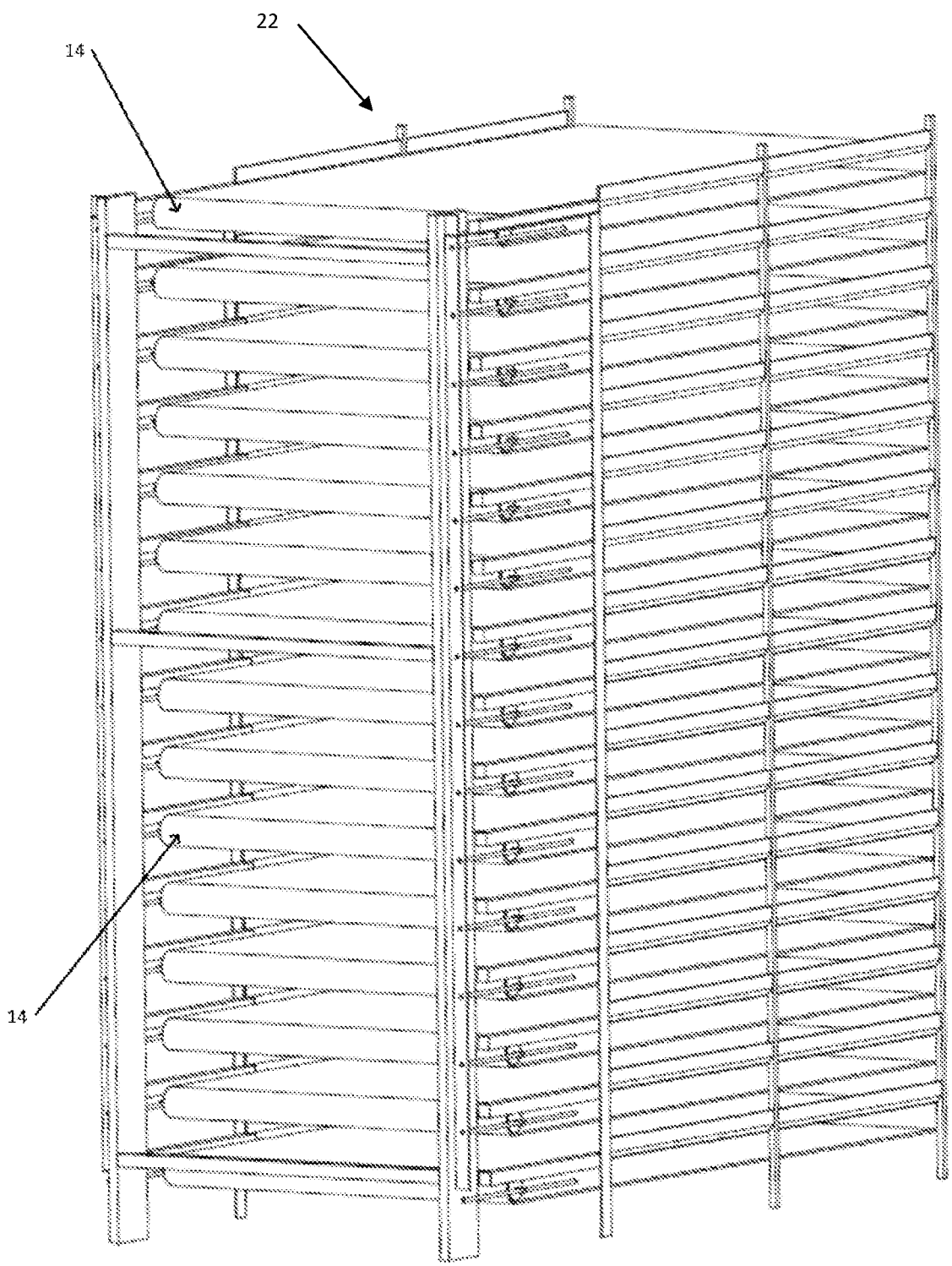
FIG. 4 shows a diagram of a storey layout of breeding lines, for clarity the flow-through feed heating and/or cooling systems are omitted from the figure, whose parts of the heating-cooling pipes are above each line or are placed under the conveyor belt.

Example 2 Production Line Comprising Feed Heating/Cooling System on a Production Line Above the Conveyor Belt In the example of embodiment of the production line (FIG. 4), the breeding line 14 was integrated with a feed heating and/or cooling system (FIG. 1), increasing the rearing efficiency by providing stable thermal conditions for the insect larvae.

Figure 8:
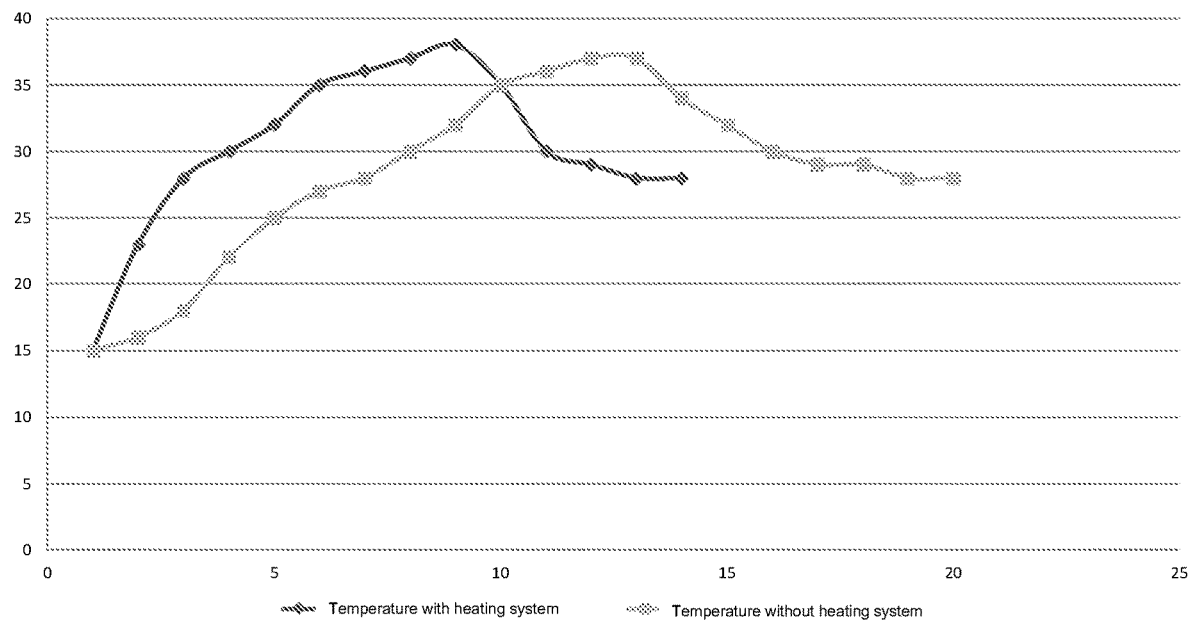
FIG. 8 shows the temperature dependence on the time of heating the feed (A), shows a cross-section of the breeding line (one storey of the breeding line that can be multi-storey) with a conveyor belt with lateral sidewalls with bending, here preferred embodiment with double bending (B).
Figure 8:
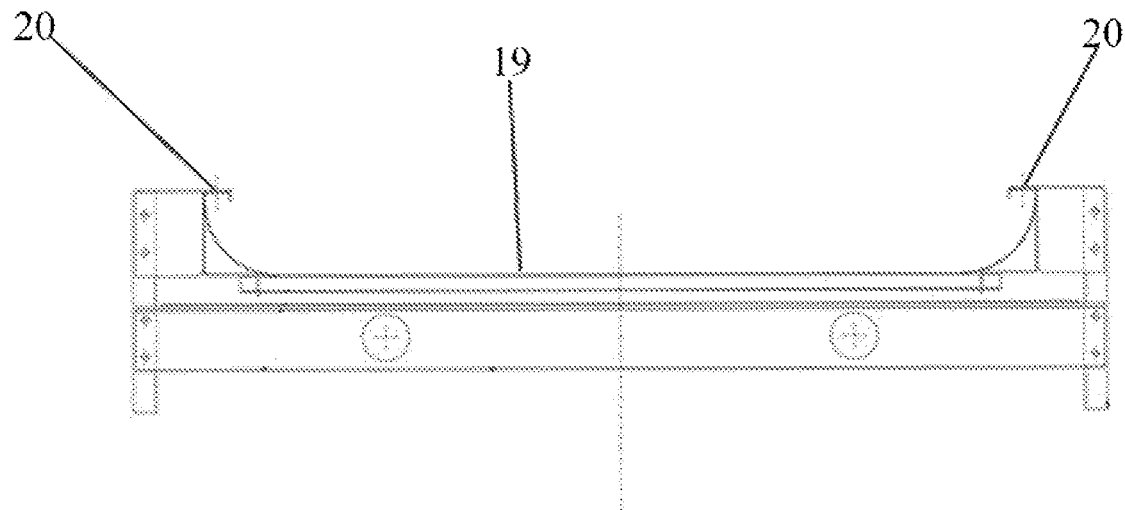
Figure 9A:
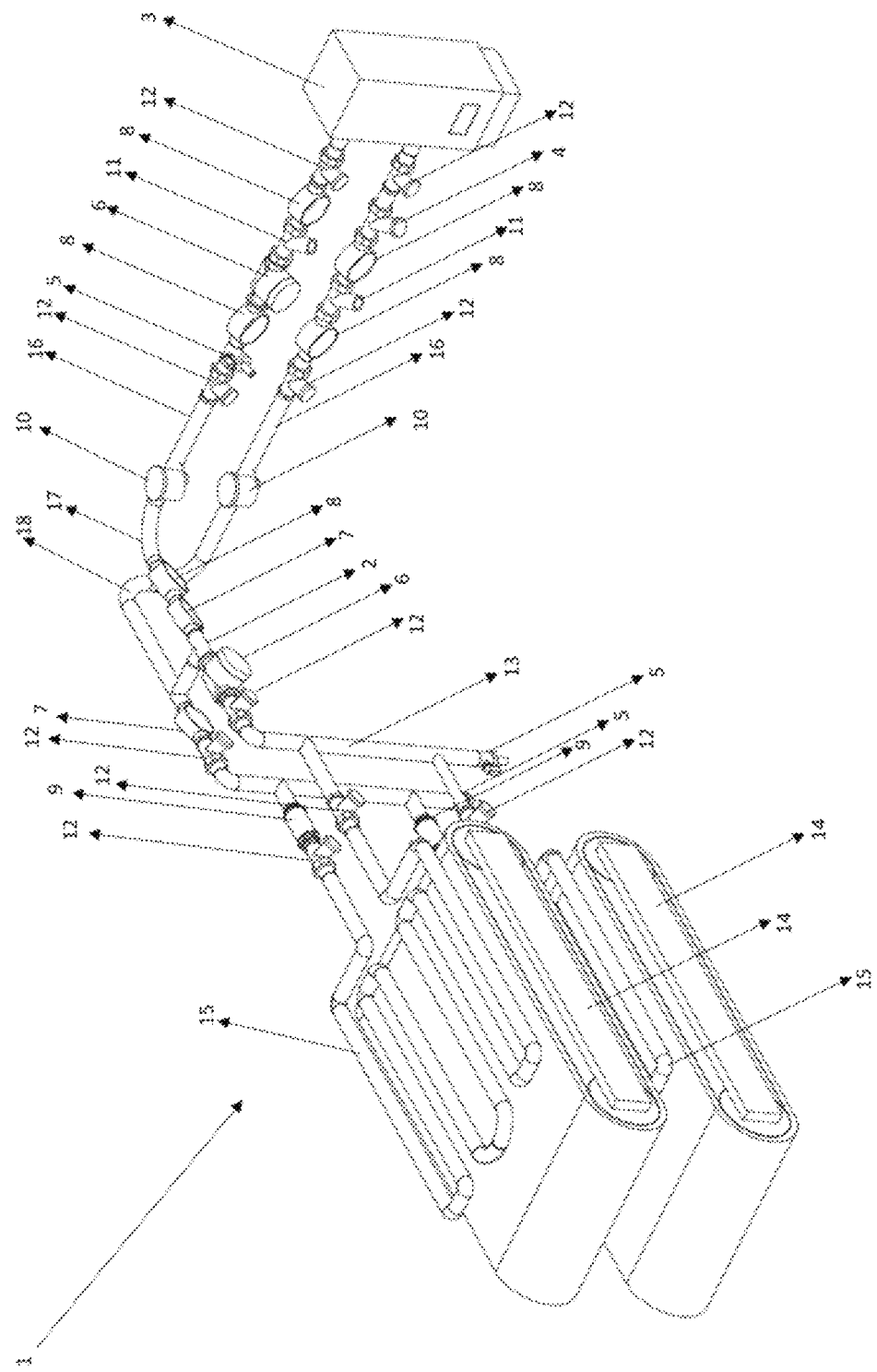
FIG. 9 shows heating-cooling pipes arranged in at least two rows on two storeys above the conveyor belt, where: 9a—combined heating and/or cooling system, 9b—heating-cooling medium supply circuit, 9c—heating-cooling medium return circuit.
Figure 9B:
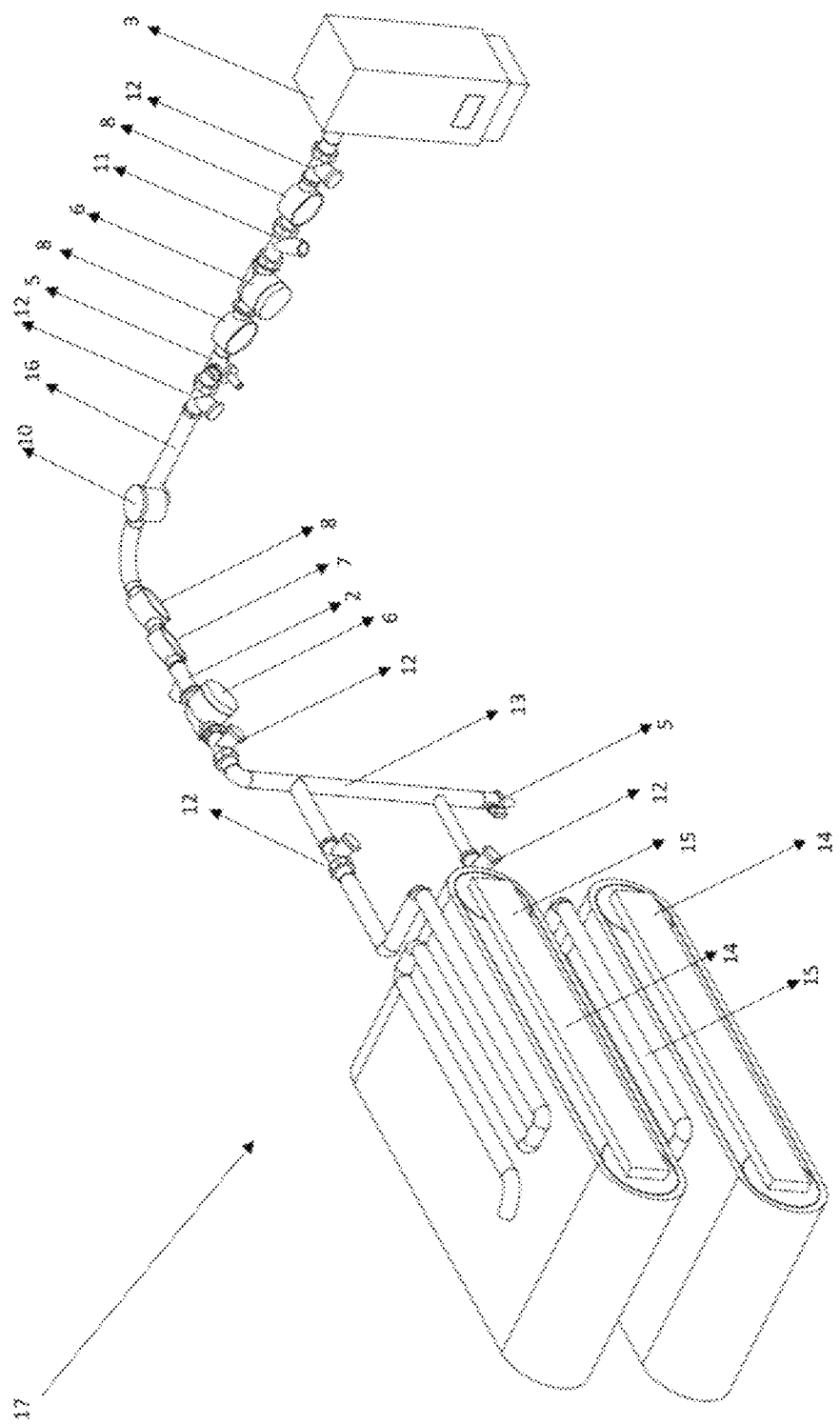
Figure 9C:
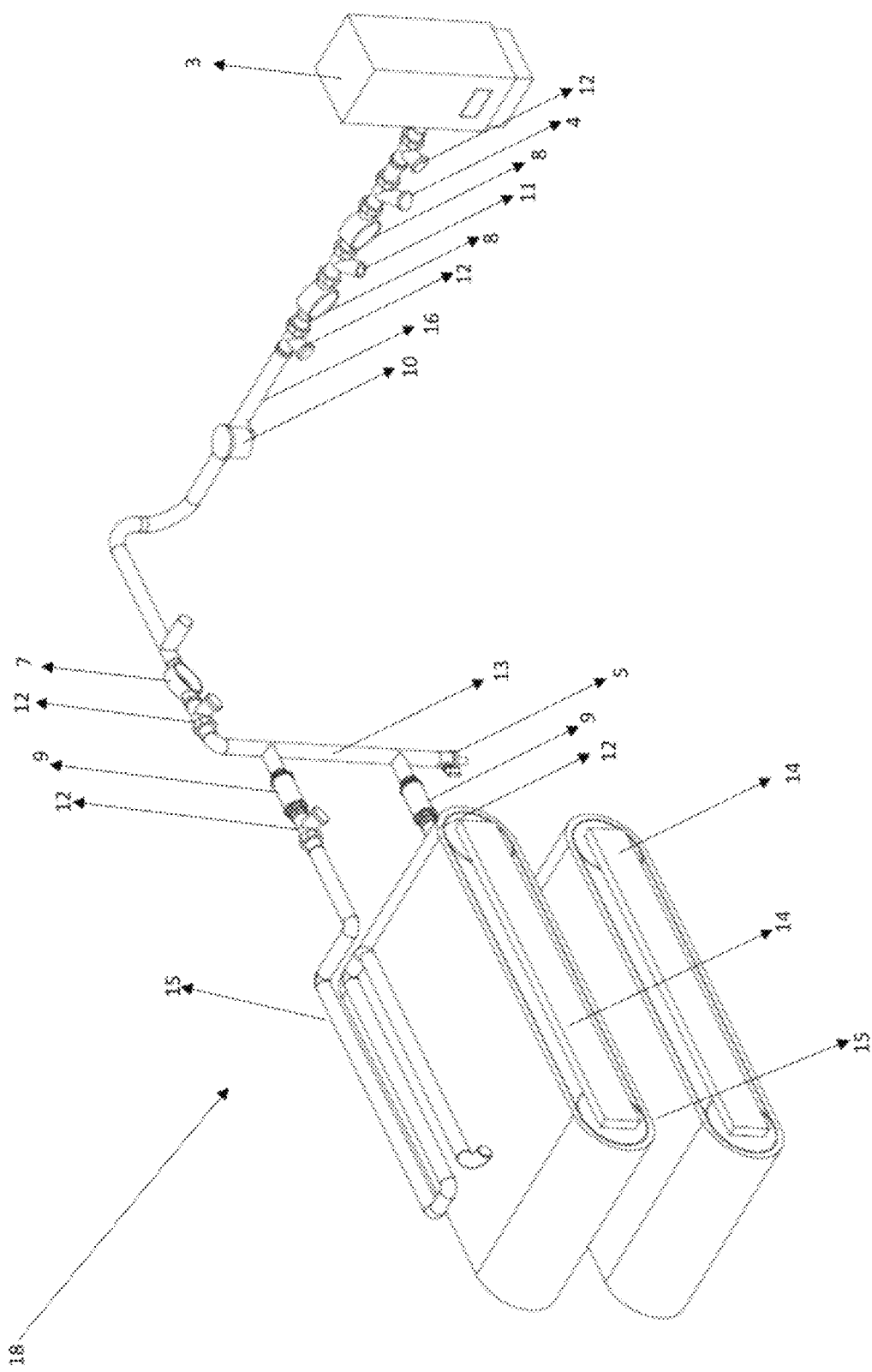
Figure 10A:
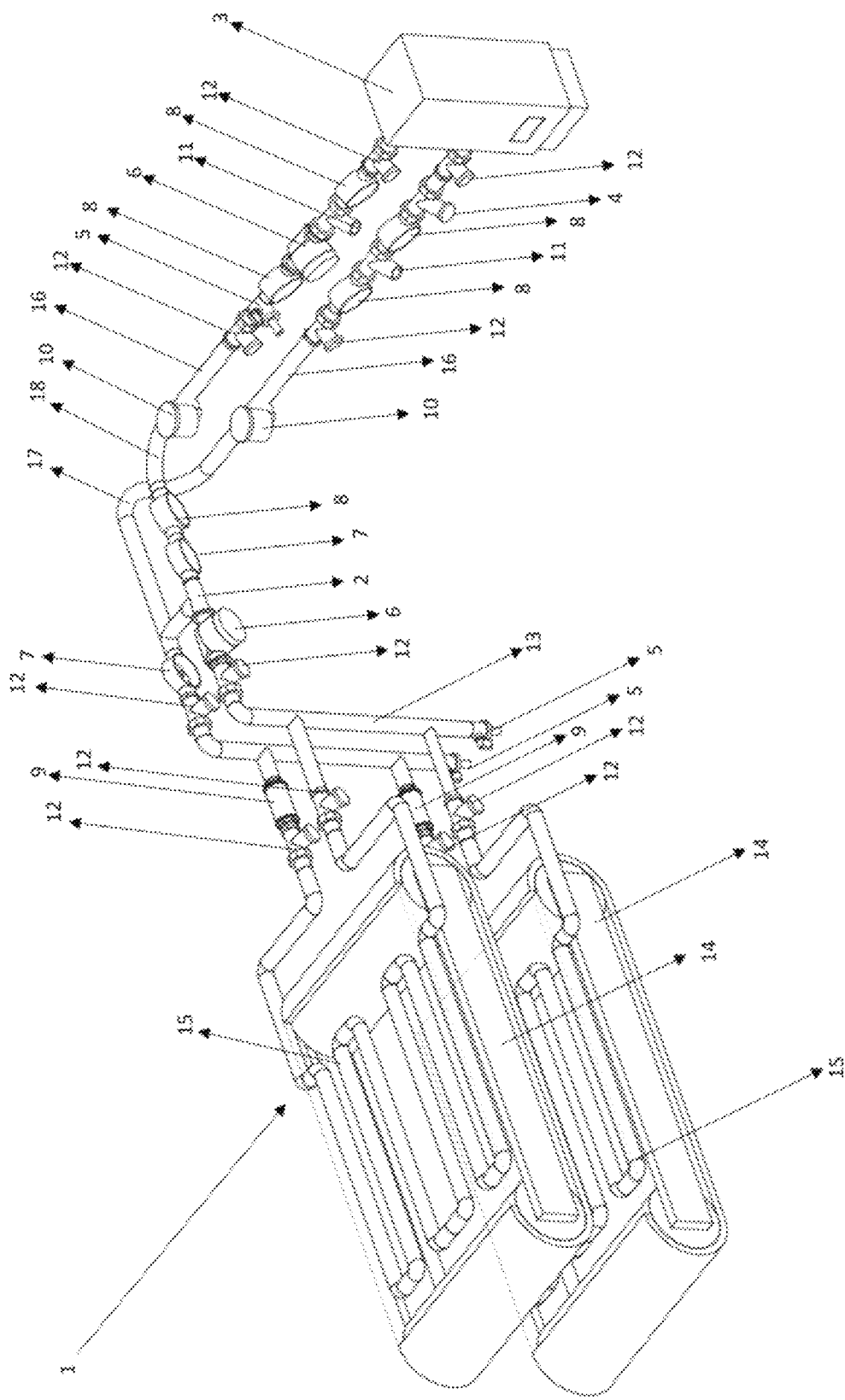
FIG. 10 Heating-cooling pipes arranged in at least two rows under the conveyor belt of a two-storey breeding line, where: 10a—combined heating and/or cooling system, 10b—heating-cooling medium supply circuit, 10c—heating-cooling medium return circuit.
Figure 10B:
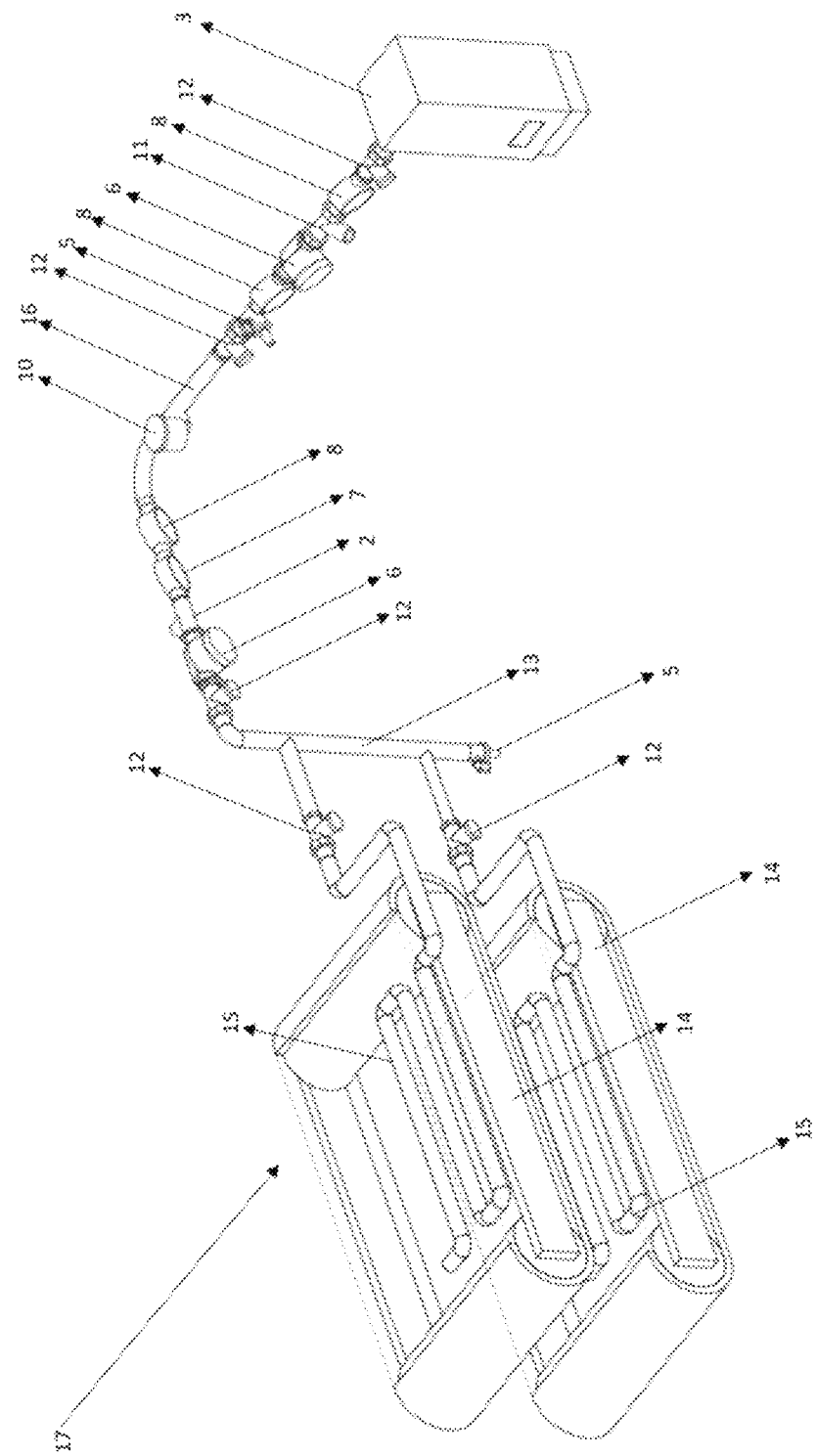
Figure 10C:
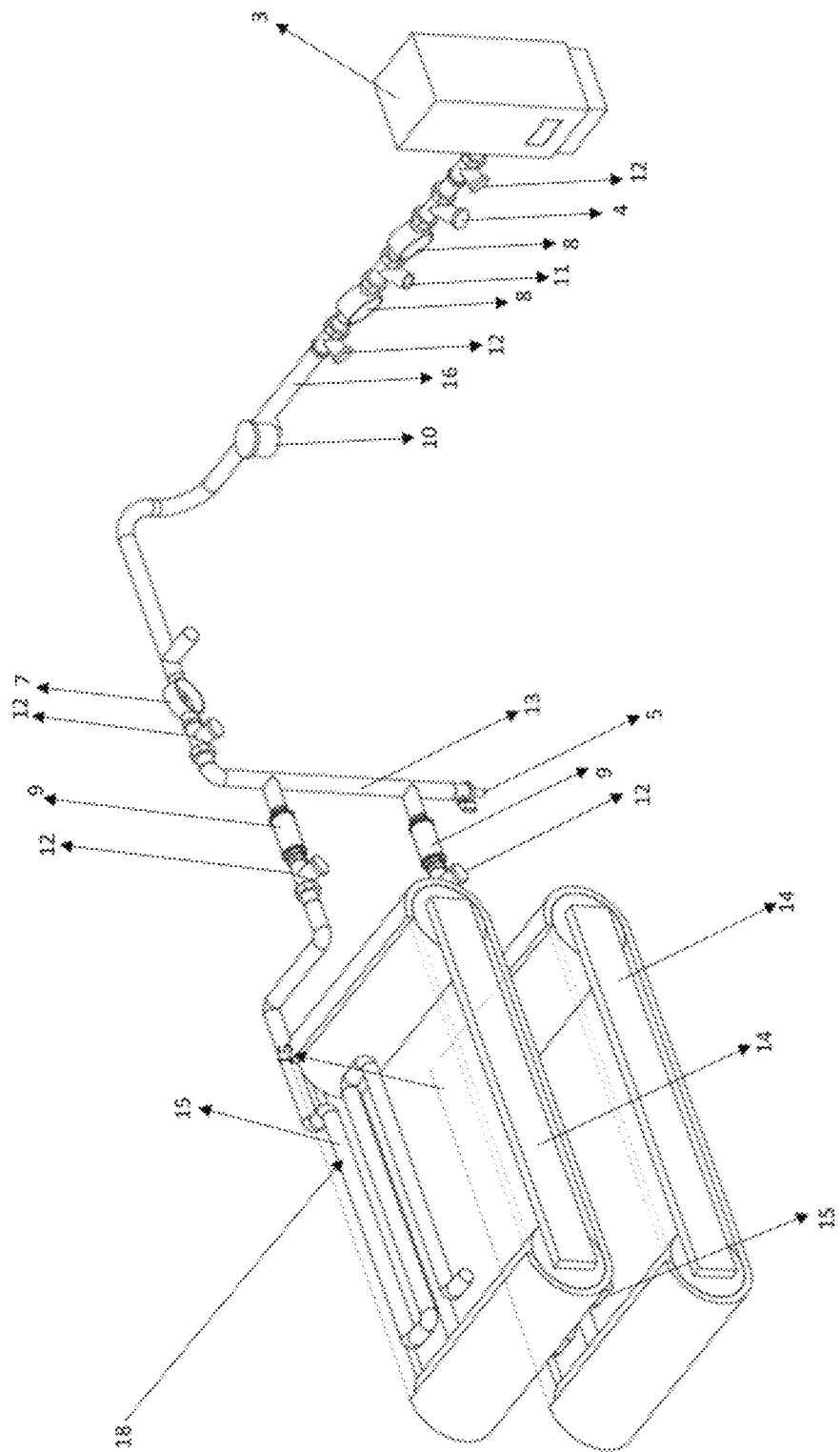

The breeding line 14 for rearing and/or breeding non-flying insects and/or larval forms of insects comprises at least one storey, which constitutes an autonomous conveyor belt 19 with profiled lateral sidewalls 20 of edges bent once or twice inwards, arranged bilaterally along the direction of movement of the conveyor belt (FIG. 8B).

Heating of the Heating-Cooling Medium

The heating-cooling medium in the system is water. The water is heated in the heat exchanger 3 in the form of a gas furnace. The temperature of water leaving the furnace is 39° C. As the heating-cooling medium, glycol can also be used. Glycol is a good medium because of its good thermal conductivity, high boiling point and low freezing point.

Transport of the Heating-Cooling Medium

The heated water is discharged from the furnace through a pipe 16 of steel placed in an insulating bundle to minimize heat loss. The intensity of water flow is 0.16 m³/h.

Heat Transfer to Feed

The heated water is fed into a distributor 13 of the heating-cooling installation, from which it is fed into a system of heating-cooling pipes 15 of PEX, which are arranged in two rows at a distance of about 20 cm from each other along the breeding lines 14 intended for rearing insects. The distance between the heating pipes 15 has been selected, so that they lie in the middle of the breeding line 14 while ensuring similar contact with the entire feed. Whereas, their arrangement in two rows is due to the fact that through each breeding line 14 a heating-cooling pipe 15 runs both, one way and the other, i.e. they form a closed loop. The water inlets to the installation of each breeding line 14 are secured by shut-off valves 12. The pipes are suspended directly above the breeding lines 14, onto which the feed for the bred insects is then laid, and more specifically above the conveyor belt 19. The laid feed has a temperature lower than the heating-cooling medium and of about 20° C. as a result of which it starts to receive its heat, until it reaches a thermal equilibrium at the level of 39° C., more preferably stabilizing the feed temperature at the level of 28-32° C. The water, cooled to a temperature of 38° C., returns through the system of heating-cooling pipes 15 and further pipes 16 to the heat exchanger 3 here the heating device.

Control of Physical Parameters

The layout of the supply of the heating-cooling medium and the receiving of the heating-cooling medium from the breeding line 14 comprise, downstream of the distributor 13, temperature sensors 7, e.g. PT-100 sensor, of the heating-cooling medium providing information about its physical parameters. The gas boiler (heat exchanger 3) is equipped with an automatic temperature regulation allowing for any temperature setting within the range from 7 to 50° C.

In the described solution, the flow-through feed heating and/or cooling system 1 is placed directly into the biomass of the insect larvae and the feed, and allows for a relatively low temperature inside the breeding rooms, because the insects assimilate the necessary heat for their development by taking up the heated food. Thus, the flow-through heating and/or cooling system for the feed being laid on the line causes indirect heating of the animals themselves.

Example 3 A Production Line Comprising a Heating and/or Cooling System of the Breeding Line Under the Belt (Heating/Cooling the Feed by Heating/Cooling the Breeding Line)

Figure 6:
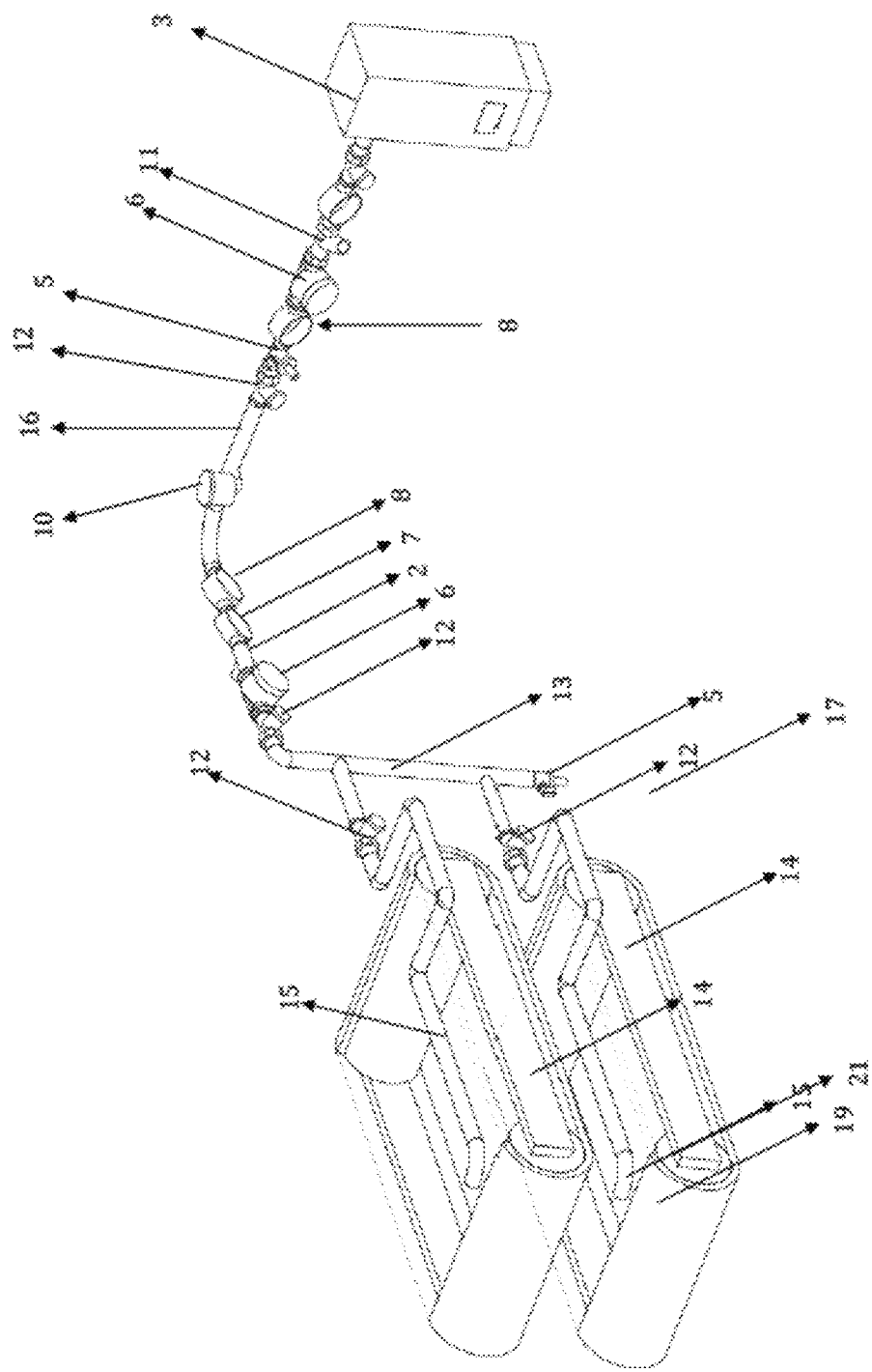
FIG. 6 shows the heated/cooled medium supply circuit of the heating and/or cooling system from FIG. 5.
Figure 7:
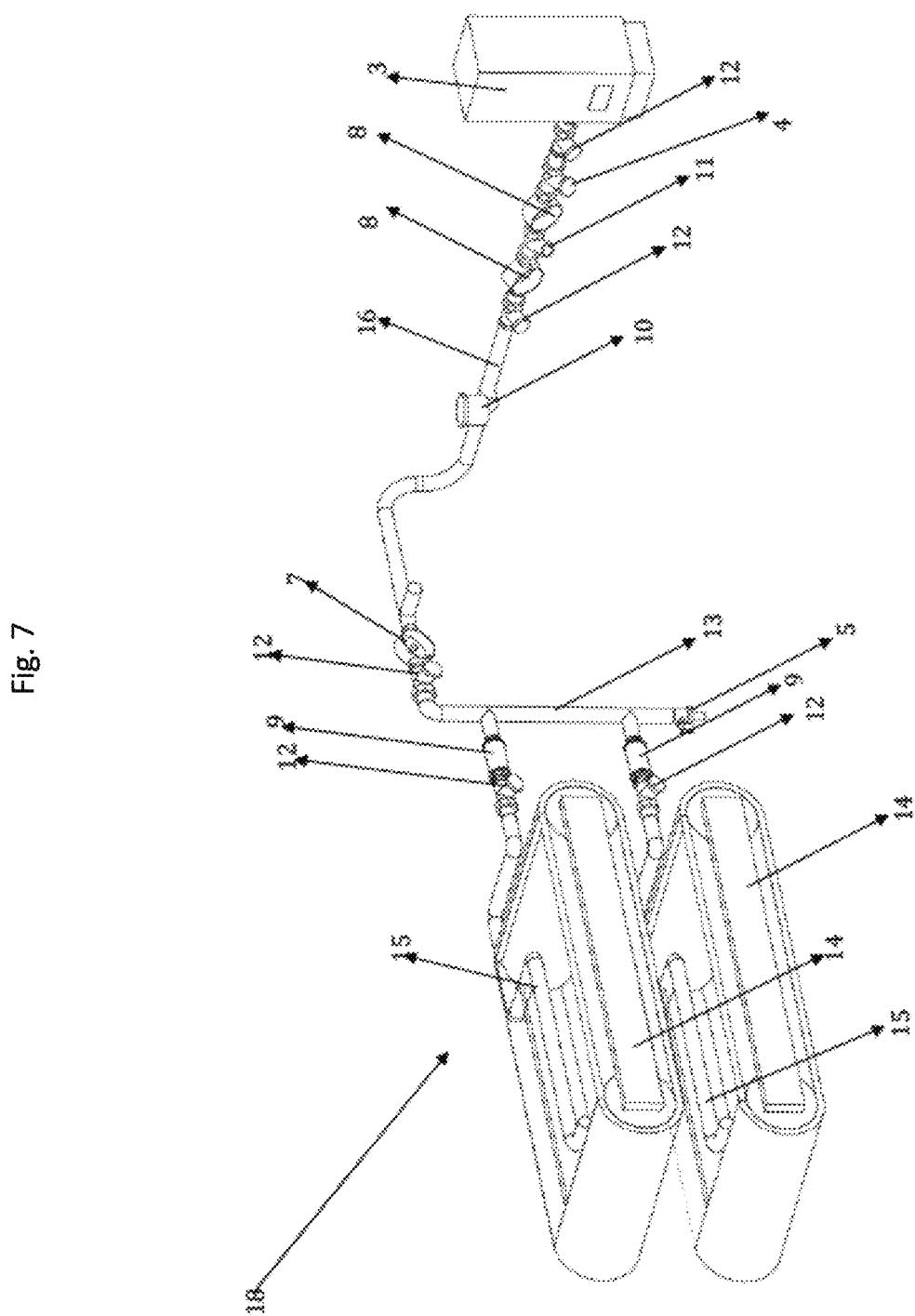
FIG. 7 shows the heated/cooled medium return circuit of the heating and/or cooling system from FIG. 5.

In this example of embodiment of the production line (FIG. 6), the breeding line 14 has been integrated with a flow-through feed heating and/or cooling system 1 (FIG. 1), increasing the rearing efficiency by providing stable thermal conditions for the insect larvae. The flow-through feed heating and/or cooling system 1 in this example of embodiment in its construction, i.e. the type of elements comprising it and the method of their connection, does not differ at all from the system described in example 1. The essential difference is that the heating-cooling pipes 15 were placed under the conveyor belt 19 of the breeding line 14. The heating-cooling pipes 15 of thermally conductive material are placed under the breeding line 14 transferring heat/cold to the breeding line 14, and the breeding line 14 heats/cools the insect biomass and the feed.

The production line comprises at least one storey of breeding line 14 for rearing and/or breeding non-flying insects and/or larval forms of insects, which constitutes an autonomous conveyor belt 19 with profiled lateral sidewalls 20 of edges bent once, preferably twice inwards, arranged bilaterally along the direction of movement of the conveyor belt.

Heating of the Heating-Cooling Medium

The heating medium in the system is water. The water is heated in the heat exchanger 3 here a gas furnace. The temperature of water leaving the furnace is 39° C. As the heating-cooling medium, glycol can also be used. Glycol is a good medium because of its good thermal conductivity, high boiling point and low freezing point.

Transport of the Heating-Cooling Medium

The heated water is discharged from the heat exchanger 3 in the form of a furnace through a pipe 16 of steel placed in an insulating bundle to minimise heat loss. The intensity of water flow is 0.16 m³/h Heat Transfer to Feed The heated water is fed into a distributor 13 of the heating-cooling installation, from which it is fed into a system of heating-cooling pipes 15 of PEX, which are arranged in two rows at a distance of about 20 cm from each other along the breeding lines 14 intended for rearing insects. The distance between the heating-cooling pipes 15 has been selected so that they lie in the middle of the breeding line 14 under the conveyor belt 19 to ensure similar contact of heat/cold with the entire feed. Whereas, their arrangement in two rows is due to the fact that through each breeding line 14 a heating-cooling pipe 15 runs both, one way and the other, i.e. they form a closed loop. The water inlets to the installation of the flow-through heating/cooling system on each breeding line 14 are secured by shut-off valves 12. The heating-cooling pipes 15 are attached by clamps to pipes or support rails directly under the conveyor belt 19 of the breeding line 14, onto which the feed for the insects to be bred is then laid. The heat from the heating-cooling medium is transferred directly to the breeding line 14. The feed laid on the line has a temperature lower than the heating-cooling medium and of 20° C. as a result of which it starts to receive its heat through the conveyor belt 19 of the heated breeding line 14, until it reaches a thermal equilibrium at the level of 39° C., more preferably stabilizing the feed temperature at the level of 28-32° C. The water, cooled to a temperature of 38° C., returns through the system of heating-cooling pipes 15 and further pipes 16 to the heating device (heat exchanger 3).

Control of Physical Parameters

The layout of the supply of the heating-cooling medium and the receiving of the heating-cooling medium from the breeding line 14 comprise, downstream of the distributor 13, temperature sensors 7, e.g. PT-100 sensor, of the heating-cooling medium providing information about its physical parameters. The gas boiler (heat exchanger 3) is equipped with an automatic temperature regulation allowing for any temperature setting within the range from 7 to 50° C.

In the described example of embodiment, the flow-through feed heating and/or cooling system is placed directly under the conveyor belt 19 of the breeding line 14, on which the biomass of the insect larvae and the feed is laid and allows for maintaining a relatively low temperature inside the breeding rooms, because the insects assimilate the necessary heat for their development by taking up the heated food. Thus, the flow-through heating and/or cooling system 1 for the feed being laid on the breeding line 14 causes indirect heating of the animals themselves.

Example 4: Use of the Flow-Through Heating and/or Cooling System for Heating and/or Cooling the Feed Tests carried out during the testing of the system have shown that the feed in the described system heats up three times faster than in the open air (when heating the breeding rooms to heat the feed and insects), which translates into effectiveness and speed of use of this system in providing appropriate thermal conditions for insects.

TABLE 1

Figure 5:
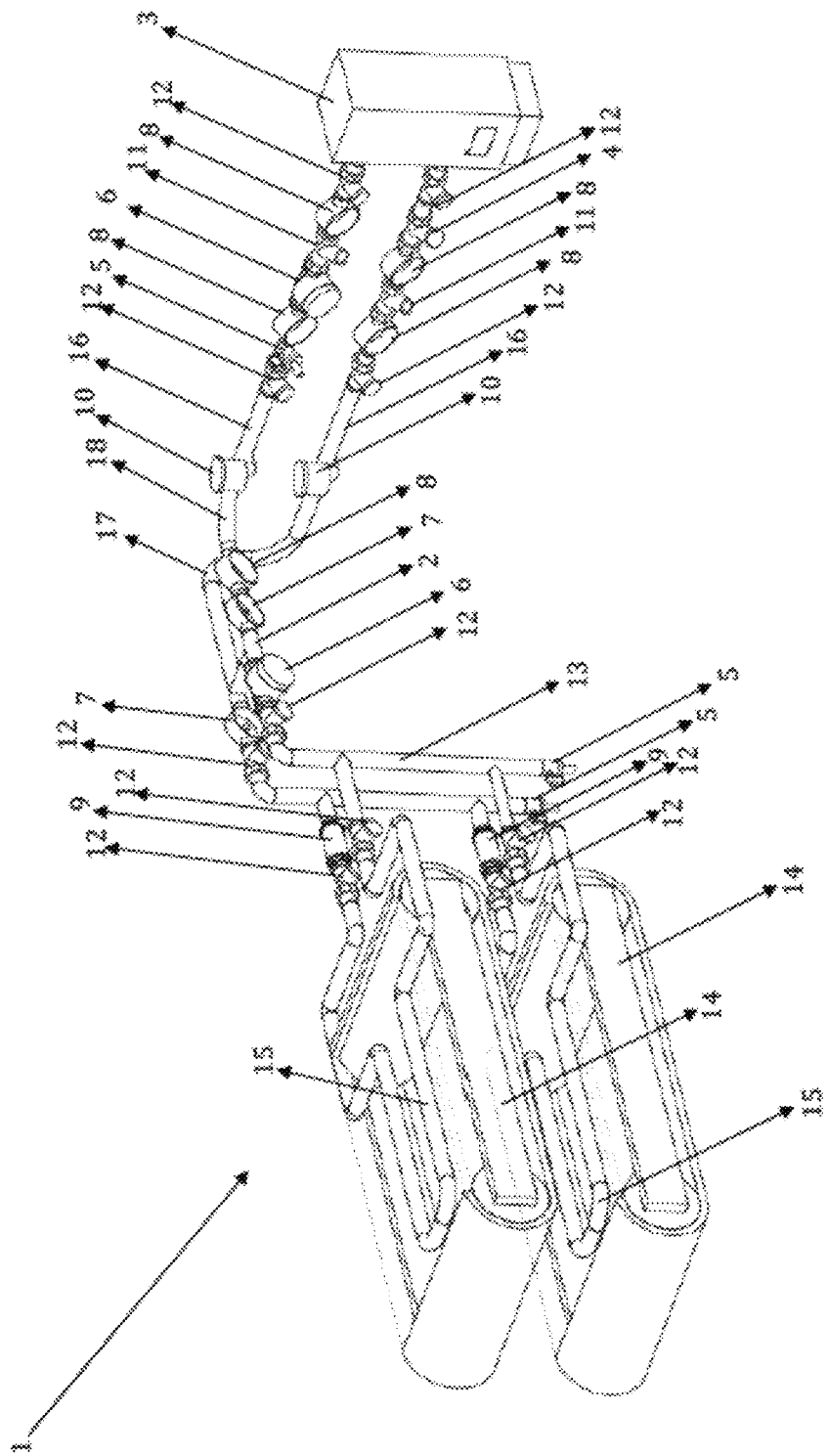
FIG. 5 shows a diagram of the flow-through heating and/or cooling system of the production line for breeding invertebrates with heating/cooling the feed on the breeding line with the system placed under the conveyor belt.

Heating the feed with and without installed system (FIG. 5)

| | | Feed temperature | |
|---|---|---|---|
| Days | Hour | With the heating system | Without the heating system |
| 0 | 06:00 | 15 | 15 |
|   | 18:00 | 23 | 16 |
| 1 | 06:00 | 28 | 18 |
|   | 18:00 | 30 | 22 |
| 2 | 06:00 | 32 | 25 |
|   | 18:00 | 35 | 27 |
| 3 | 06:00 | 36 | 28 |
|   | 18:00 | 37 | 30 |
| 4 | 06:00 | 38 | 32 |
|   | 18:00 | 35 | 35 |
| 5 | 06:00 | 30 | 36 |
|   | 18:00 | 29 | 37 |
| 6 | 06:00 | 28 | 37 |
|   | 18:00 | 28 | 34 |
| 7 | 06:00 |  | 32 |
|   | 18:00 |  | 30 |
| 8 | 06:00 |  | 29 |
|   | 18:00 |  | 29 |
| 9 | 06:00 |  | 28 |
|   | 18:00 |  | 28 |

TABLE 2

Summary of results for heating the feed

| Type of feed | With feed heating Fruit and vegetable mix | No feed heating Fruit and vegetable mix |
|---|---|---|
| Layer thickness | 5-7 cm | 5-7 cm |
| Heating duration | 6 days | 9 days |

Example 5: Comparative Measurement of Body Weight of Bred Insects and Feed Conversion Ratio Comparative measurements were carried out using the breeding method according to the invention and known breeding methods with and without heating the feed on the breeding line 14.

Insects bred using the described breeding method of heating and/or cooling of the feed on the breeding line according to the invention are characterized by a 25% faster fattening, achieving a 7.5% higher body weight at the end of the fattening, as well as a reduction of up to 12% in the feed conversion ratio (FCR).

TABLE 3

Results of an insect rearing experiment on lines with heating the feed and without it.

| Type of feed | Feed heating Fruit and vegetable mix | No feed heating Fruit and vegetable mix |
|---|---|---|
| Insect species | H. illucens | H. illucens |
| BWG kg/m² | 6.42 | 5.97 |
| FCR | 6.8 | 7.77 |
| Survival | 93% | 52% |
| Rearing time | 6 | 8 |

Example 6: Use of the Flow-Through Feed Heating and/or Cooling System on the Breeding Line for Cooling the Feed Tests carried out during the testing of the system have shown that the feed, and thus the insects feeding on it, in the case of excessively high temperatures, cools down more quickly with the use of a flow-through heating and/or cooling system for cooling the feed than in the open air with the use of a cooling system where breeding takes place, which translates into efficiency and speed of use of this system in ensuring appropriate and stabilized close to optimal thermal conditions for the insects, as well as cooling them down in this way and avoiding overheating, removing excess metabolic heat excreted by the insects or even killing them due to excessively high temperatures.

TABLE 4

Cooling the feed with and without installed flow-through feed heating/cooling system in the breeding line (cooling of breeding rooms).

| | | Temperature | |
|---|---|---|---|
| Days | Hour | With cooling system | Without cooling system |
| 1 | 06:00 | 38 | 38 |
|   | 18:00 | 35 | 38 |
| 2 | 06:00 | 30 | 37 |
|   | 18:00 | 29 | 37 |
| 3 | 06:00 | 28 | 36 |
|   | 18:00 | 28 | 34 |
| 4 | 06:00 | 28 | 32 |
|   | 18:00 | 28 | 31 |
| 5 | 06:00 |    | 30 |
|   | 18:00 |    | 30 |
| 6 | 06:00 |    | 29 |
|   | 18:00 |    | 28 |
| 7 | 06:00 |    | 28 |
|   | 18:00 |    | 28 |

TABLE 5

Summary of results for cooling the feed

| Type of feed | With feed cooling mix. Fruit and vegetable | No feed cooling mix. Fruit and vegetable |
|---|---|---|
| Layer thickness | 5-7 cm | 5-7 cm |
| Cooling duration | 2 days | 5.5 days |

Example 7: Measurement of Insect Survival

Insects bred using the method according to the invention with the use of a flow-through feed heating and/or cooling system on the breeding line were provided with optimised and stable temperature conditions, which resulted in reduced larval feeding stress and increased larval survival, which was observed to be up to 45% higher with the use of a flow-through heating and/or cooling system 1 compared to the standard rearing method, where entire holding rooms are heated/cooled (Table 3). Similar results of increased survival were obtained with cooling the feed.

Example 8: Drying of Fertiliser

In this example of embodiment (Tab. 6 and Tab. 7), the use of a feed heating and/or cooling system on the line for the drying of secondary metabolites after insect production including faeces, which are a component of fertiliser, is shown in comparison to heating the breeding rooms.

TABLE 6

Results of experiment showing drying of faeces (fertiliser)

| | Feed moisture | |
|---|---|---|
| Rearing days | Heating system % dry mass | No heating % dry mass |
| 1 | 25 | 25 |
| 2 | 30 | 27 |
| 3 | 40 | 30 |
| 4 | 60 | 35 |
| 5 | 70 | 40 |
| 6 | 80 | 50 |
| 7 |    | 60 |
| 8 |    | 70 |
| 9 |    | 80 |
| 10 |   |    |

TABLE 7

Summary of results for drying of fertiliser

| | Feed heating | No feed heating |
|---|---|---|
| Start moisture | 25% dry mass | 25% dry mass |
| Final moisture | 80% dry mass | 80% dry mass |
| Type of feed | mix. Fruit and vegetable | mix. Fruit and vegetable |
| Layer thickness | 5-7 cm | 5-7 cm |
| Heating duration | 6 days | 9 days |

Example 8: Construction of an Electrical Feed Heating System on the Breeding Line for Insect Breeding and Rearing A heated production surface for rearing and/or breeding insects and/or larval forms of insects with an electrical feed heating system on a production line 14 for heating feed in insect breeding is shown in FIG. 11 and comprises an electrical feed heating system 22 comprising a heating cable 23 placed on and/or under the surface of the breeding line 14 such that direct contact with the feed or indirect contact is provided through the surface of the breeding line 14 for heating the feed laid thereon. The method of placing the heating cable 23 on and/or under the surface of the breeding line is known in the field of construction. It should be made clear, for the sake of clarity, that by breeding line 14 is meant the surface/substrate on which insect breeding is carried out. The construction of the line, in terms of construction, is of any design, but with the condition that the breeding line 14 conducts heat well in the case where the heating cable is laid under the surface of the breeding line. In this case, the material of which the breeding line is made at the place of direct contact with the breeding mass (feed and insects) which is to be heated by the electric heating system 22 should provide good thermally conductive properties. The breeding line 14 may also be made entirely of such material.

It is preferred that the breeding line 14 is made of metal, e.g. copper, steel or aluminium, plastic, ceramic or concrete. Stainless steel appears to be a preferred embodiment because of its ease of cleaning, its approval for contact with food and feed materials and its relatively low operating costs. In a preferred example of embodiment, the breeding line is in the form of a conveyor belt 19. In a preferred embodiment, the breeding line 14 is provided with sidewalls 20 to ensure bio-assurance.

The electrical feed heating system 22 on the breeding line 14 for heating feed for insect breeding and rearing comprises the following construction elements:

heating cable 23 placed on and/or under the surface of the breeding line 14;
connection wires 24;
feed temperature sensor 25 on the breeding line;
control-power unit 26, which powers the heating cable and controls the operation of the heating cable.

In order to transfer the heat to the feed, the heating cable 23 is powered by a current with predetermined parameters (voltage, frequency, amperage) controlled by the control-power unit 26 on the basis of data received from the feed temperature sensor 25. The control-power unit 26 is powered by an external power source coming from the mains or a battery or a power generator. The control-power unit 26 is connected to the heating cable 23 via connection wires 24. The control-power unit allows to automatically change the parameters of the outgoing current in order to maintain the temperature of the heating cable within a predetermined temperature range from 7 to 50° C., preferably 20° C.-48° C., more preferably to 25-35° C., more preferably to 28-32° C. or other or zonally different.

The electrical feed heating system 22 on the breeding line constituting a part heating the feed for rearing and/or breeding insects and/or larval forms of insects may also comprise multiple layouts of heating cables and the cables may be routed to more than one breeding line.

When using an electrical feed heating system 22 on the breeding line 14, the same results were obtained as in the case of a flow-through feed heating and/or cooling system with a closed flow of the heating-cooling medium, included in Tab. 3, 6, 7. The use of an electrical feed heating system on the line allows to heat the feed to the desired temperature and stabilize it within the selected temperature range so as to ensure optimum breeding conditions for a given insect species, thus ensuring the optimal thermal conditions for insects rearing as well as allow drying of secondary metabolites after insect production including faeces, which are a component of the fertilizer.

REFERENCES

1—a flow-through feed heating and/or cooling system on a production line
2—three-way valve
3—heat exchanger
4—balancing valve
5—drain valve
6—circulation pump
7—temperature sensor
8—pressure sensor
9—rotameter
10—vent
11—solid particle filter
12—shut-off valves
13—distributor
14—breeding line
15—heating-cooling pipes (e.g. PEX pipes)
16—pipes e.g. steel pipes
17—heating medium supply circuit
18—heating medium return circuit
19—conveyor belt
20—lateral sidewalls
21—drive shafts for the conveyor belt
22—electrical feed heating system on a breeding line
23—heating cable
24—connection wires
25—feed temperature sensor
26—control-power unit

What is claimed is:

1. A production line for rearing and/or breeding insects and/or larval forms of insects, comprising:
   a) at least one breeding line (14) for breeding insects and for laying a feed thereon,
   b) a flow-through feed heating and/or cooling system (1) with a closed flow of a heating-cooling medium for heating and/or cooling the feed on the at least one breeding line (14),
   wherein the heating and/or cooling system (1) with a closed flow comprises at least one heating-cooling medium supply circuit (17) and at least one heating-cooling medium return circuit (18) connected to each other, and the heating-cooling medium supply circuit (17) and the heating-cooling medium return circuit (18) are fluidly connected to a heat exchanger (3) for heating/cooling the heating-cooling medium, and the heating-cooling medium supply circuit (17) and the heating-cooling medium return circuit (18) comprise distributors (13) for the heating-cooling medium, and to the heating-cooling medium distributor (13) via a shut-off valve (12), heating-cooling pipes (15) of thermally conductive material are connected for the distribution of heat and/or cold on the at least one breeding line (14),
   wherein the heating-cooling pipes (15) of thermally conductive material of the feed heating/cooling system on the at least one breeding line (14) are arranged parallel to an autonomous conveyor belt (19) of the at least one breeding line (14) for laying feed for breeding insects thereon,
   wherein the heating-cooling pipes (15) of thermally conductive material are arranged along the at least one breeding line (14) for rearing insects and are arranged in at least two rows parallel to each other,
   wherein the heating-cooling medium supply circuit (17) and the heating-cooling medium return circuit (18) are connected via a three-way valve (2), wherein the rearing and/or breeding of insects and/or larval forms of insects concern insects of the orders Coleoptera and/or Diptera.

2. The production line according to claim 1,
   wherein the at least one breeding line (14) comprises at least one storey, which constitutes the autonomous conveyor belt (19), with profiled lateral sidewalls (20) arranged bilaterally along the direction of movement of the conveyor belt (19), the edges of the lateral sidewalls (20) are bent inwards; and
   wherein the heating-cooling medium is water or glycol.

3. The production line according to claim 1,
   wherein the production line comprises two to, thirty storeys comprising the at least one breeding line (14) with a flow-through feed heating and/or cooling system with a closed flow of the heating/cooling medium.

4. The production line according to claim 1, wherein
   the heat exchanger (3) provides heating/cooling of the heating-cooling medium to a temperature in the range of 7-50° C.; and
   the heat exchanger (3) is based on a source of electrical energy, gas or the use of heat pumps or heat recuperation.

5. The production line according to claim 1, wherein
the heating-cooling pipes (15) are made of a material with good thermally conductive properties including copper, steel, aluminum, or synthetic material;
the heating-cooling pipes (15) arranged on and/or under the conveyor belt (19) of the at least one breeding line (14) form at least two rows of heating-cooling pipes (15) spaced from each other by 20 cm; and
the fluid connection is provided by pipes (16) made of steel.

6. The production line according to claim 1, wherein,
the heating-cooling medium supply circuit (17) and the heating-cooling medium return circuit (18) comprise a system of shut-off valves (12), drain valves (5), vents (10), at least one temperature sensor (7) and at least one pressure sensor (8), which are fluidly connected to each other;
the heating-cooling medium return circuit (18) comprises a rotameter (9); and
the heating-cooling medium supply circuit (17) comprises a solid particle filter (11).

7. The production line according to claim 1, whereby the rearing and/or breeding of insects and/or larval forms of insects are achieved.

8. A method for breeding insects, comprising the steps of:
a) laying a feed at the storage temperature on at least one breeding line (14) adapted for laying feed for breeding insects,
b) heating and/or cooling the feed for insects laid on at least one breeding line (14) adapted for laying feed for insects thereon by a flow-through feed heating and/or cooling system (1) with a closed flow for heating and/or cooling the feed on the at least one breeding line (14), and
wherein the flow-through feed heating and/or cooling system (1) includes:
at least one heating-cooling medium supply circuit (17) and at least one heating-cooling medium return circuit (18) connected to each other, and the heating-cooling medium supply circuit (17) and the heating-cooling medium return circuit (18) are fluidly connected to a heat exchanger (3) for heating/cooling the heating-cooling medium, and the heating-cooling medium supply circuit (17) and the heating-cooling medium return circuit (18) comprise distributors (13) of the heating-cooling medium, and to the heating-cooling medium distributor (13) via a shut-off valve (12) heating-cooling pipes (15) of thermally conductive material are connected for the distribution of heat/cold on the at least one breeding line (14),
wherein the heating-cooling pipes (15) are arranged parallel to the said at least one breeding line (14) for laying feed for breeding insects thereon,
wherein the heating-cooling pipes (15) of thermally conductive material are arranged along the at least one breeding line (14) for rearing insects and are arranged in at least two rows parallel to each other, wherein the heating-cooling medium supply circuit (17) and the heating-cooling medium return circuit (18) are connected via a three-way valve (2),
wherein the rearing and/or breeding of insects and/or larval forms of insects concern insects of the orders Coleoptera and/or Diptera.

9. The method for breeding insects according to claim 8, wherein the at least one breeding line (14) comprises at least one storey, which constitutes an autonomous conveyor belt (19), with profiled lateral sidewalls (20) arranged bilaterally along the direction of movement of the conveyor belt (19), the edges of the lateral sidewalls (20) are bent inwards, and
wherein the heating-cooling medium in the flow-through feed heating and/or cooling system (1) is water or glycol;
wherein the feed is heated/cooled to a temperature in the range of 7-50° C.;
wherein heat exchanger (3) provides heating/cooling of the heating-cooling medium to a temperature in the range of 7-50° C.;
wherein the heat exchanger (3) is based on an electrical or gas energy source or the use of heat pumps or heat recuperation;
wherein the heating-cooling pipes (15) are made of a material with good thermally conductive properties including copper, steel, aluminum, synthetic material; and
wherein the fluid connection is provided by pipes (16) made of steel.

10. The method for breeding insects according to claim 8, in the flow-through feed heating and/or cooling system (1), the heating-cooling medium supply circuit (17) and the heating-cooling medium return circuit (18) include a system of shut-off valves (12), drain valves (5), vents (10), at least one temperature sensor (7), and at least one pressure sensor (8) are fluidly connected to each other;
wherein the heating-cooling medium return circuit (17) includes a rotameter (9); and
wherein heating-cooling medium supply circuit (18) includes a solid particle filter (11).

11. The method for breeding insects according to claim 8, further comprising the step of placing the bred insects in drawer, box, or self-supporting systems.

12. The method for breeding insects according to claim 8, wherein in the flow-through feed heating and/or cooling system (1):
at least one storey including the at least one breeding line (14) and a flow-through heating and/or cooling system (1) with a closed flow of the heating/cooling medium;
wherein the at least one breeding line (14) comprises at least one storey, which constitutes an autonomous conveyor belt (19), and
wherein the heating-cooling pipes (15) are arranged on and/or under the conveyor belt (19) of the at least one breeding line (14) and form at least two rows of heating-cooling pipes (15) spaced from each other, preferably by 20 cm.

13. The method for breeding insects according to claim 8, wherein the feed heating system comprises an electrical feed heating system (22) on a breeding line placed on and/or under the surface of the at least one breeding line (14),
wherein the electrical heating system (22) of the breeding line comprises a heating cable (23) placed on and/or under the at least one breeding line (14) in such a way as to heat the feed,
wherein the heating cable (23) is connected via connection wires (24) to a control-power unit (26) controlling the operation of the heating cable, said control-power unit (26) being connected to an energy source; and
wherein the electrical feed heating system (22) is selected from a heating mat or heating cable.

14. A flow-through feed heating and/or cooling system with a closed flow, comprising:
a breeding line (14) for breeding insects, wherein said flow-through feed heating and/or cooling system (1)

includes at least one heating-cooling medium supply circuit (17) and at least one heating-cooling medium return circuit connected to each other, and the heating-cooling medium supply circuit (17) and the heating-cooling medium return circuit (18) are fluidly connected with a heat exchanger (3) for heating/cooling the heating-cooling medium, and the heating-cooling medium supply circuit (17) and the heating-cooling medium return circuit (18) comprise heating-cooling medium distributors (13), and heating-cooling pipes (15) of thermally conductive material for distribution of heat/cooling on the breeding line (14) are connected to the heating-cooling medium distributor (13) via a shut-off valve (12), wherein the heating-cooling pipes (15) of thermally conductive material for distribution of heat/cooling on the breeding line (14) are arranged parallel to an autonomous conveyor belt (19) said at least one breeding line (14) for laying feed for breeding insects thereon, wherein the heating-cooling pipes (15) of thermally conductive material are arranged along the breeding line (14) for rearing insects and are arranged in at least two rows parallel to each other, wherein the heating-cooling medium supply circuit (17) and the heating-cooling medium return circuit (18) are connected via a three-way valve (2), wherein the rearing and/or breeding of insects and/or larval forms of insects concern insects of the orders Coleoptera and/or Diptera; and wherein the heating-cooling pipes (15) are arranged on and/or under the conveyor belt (19) of the breeding line (14) and form at least two rows of heating-cooling pipes (15) spaced from each other, by 20 cm.

15. The system according to claim 14, wherein the breeding line (14) comprises at least one storey, which constitutes the autonomous conveyor belt (19), wherein the heating-cooling medium is water or glycol, and wherein system comprises two to thirty storeys comprising the breeding line (14) with a flow-through feed heating and/or cooling system with a closed flow of the heating/cooling medium.

16. The system according to claim 14, wherein:

the heat exchanger (3) provides heating/cooling of the heating-cooling medium to a temperature in the range of 7-50 ° C.;

the heat exchanger (3) is based on an electrical or gas energy source or the use of heat pumps or heat recuperation;

the heating-cooling pipes (15) are made of a material with good thermally conductive properties, including copper, steel, aluminum, or a synthetic material; and the fluid connection is provided by pipes (16) made of steel.

17. The system according to claim 14, wherein:

the heating-cooling medium supply circuit (17) and the heating-cooling medium return circuit (18) include a system of shut-off valves (12), drain valves (5), vents (10), at least one temperature sensor (7) and at least one pressure sensor (8), and are fluidly connected to each other;

the heating-cooling medium return circuit includes a rotameter (9); and the heating-cooling medium supply circuit includes a solid particle filter (11).

* * * * *